US009889198B2

(12) United States Patent
Mickle et al.

(10) Patent No.: US 9,889,198 B2
(45) Date of Patent: *Feb. 13, 2018

(54) FATTY ACID CONJUGATES OF QUETIAPINE, PROCESS FOR MAKING AND USING THE SAME

(71) Applicant: KemPharm, Inc., Coralville, IA (US)

(72) Inventors: Travis Mickle, Kissimmee, FL (US); Sven Guenther, Coralville, IA (US); Sanjib Bera, Blacksburg, VA (US)

(73) Assignee: KemPharm, Inc., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,336

(22) Filed: May 15, 2017

(65) Prior Publication Data
US 2017/0246301 A1 Aug. 31, 2017

Related U.S. Application Data

(60) Continuation of application No. 15/340,533, filed on Nov. 1, 2016, which is a division of application No. 14/525,836, filed on Oct. 28, 2014, now Pat. No. 9,511,149, which is a continuation of application No. 13/581,496, filed as application No. PCT/US2011/027658 on Mar. 9, 2011, now Pat. No. 8,900,604.

(60) Provisional application No. 61/312,977, filed on Mar. 11, 2010.

(51) Int. Cl.
A61K 45/06 (2006.01)
A61K 31/554 (2006.01)
A61K 39/39 (2006.01)
A61K 9/00 (2006.01)
C07D 417/04 (2006.01)
A61K 47/48 (2006.01)

(52) U.S. Cl.
CPC .......... A61K 45/06 (2013.01); A61K 9/0053 (2013.01); A61K 31/554 (2013.01); A61K 39/39 (2013.01); A61K 47/48038 (2013.01); A61K 47/48046 (2013.01); C07D 417/04 (2013.01)

(58) Field of Classification Search
CPC .......... A61K 47/48038; A61K 31/554; C07D 417/04
See application file for complete search history.

(56) References Cited

U.S. PATENT DOCUMENTS

| 4,064,138 A | 12/1977 | Saari et al. |
| 4,879,288 A | 11/1989 | Warawa et al. |
| 5,527,797 A | 6/1996 | Eisenberg et al. |
| 5,603,959 A | 2/1997 | Horrobin et al. |
| 5,955,459 A | 9/1999 | Bradley et al. |
| 6,022,955 A | 2/2000 | Sarin et al. |
| 6,197,764 B1 | 3/2001 | Sarin et al. |
| 6,599,897 B1 | 7/2003 | Brown |
| 6,623,752 B1 | 9/2003 | Fischer et al. |
| 7,060,708 B2 | 6/2006 | Piccariello et al. |
| 9,597,403 B2 | 3/2017 | Mickle et al. |
| 2003/0109419 A1 | 6/2003 | Greengard et al. |
| 2004/0242570 A1 | 12/2004 | Nudelman et al. |
| 2005/0026899 A1 | 2/2005 | Goldstein et al. |
| 2005/0026900 A1 | 2/2005 | Goldstein et al. |
| 2005/0171088 A1 | 8/2005 | Ault et al. |
| 2006/0025567 A1 | 2/2006 | Collins et al. |
| 2007/0225379 A1 | 9/2007 | Carrara et al. |
| 2007/0244093 A1 | 10/2007 | Boehm et al. |
| 2008/0139649 A1 | 6/2008 | Barrow et al. |
| 2009/0042955 A1 | 2/2009 | Lynch et al. |
| 2009/0131525 A1 | 5/2009 | Mickle et al. |
| 2009/0131534 A1 | 5/2009 | Mickle et al. |
| 2009/0137672 A1 | 5/2009 | Mickle et al. |
| 2011/0183963 A1 | 7/2011 | Mickle et al. |

FOREIGN PATENT DOCUMENTS

| WO | 03026563 | 4/2003 |
| WO | 2003079972 | 10/2003 |
| WO | 2007004236 | 1/2007 |
| WO | 2008050341 | 5/2008 |
| WO | 2008079838 | 7/2008 |

OTHER PUBLICATIONS

Cameron et al., Potential Role of a Quetiapine Metabolite in Quetiapine-Induced Neutropenia and Agranuocytosis, Chem. Res. Tocicol, 2012, 25, p. 1004-1011 and references cited therein.
Cole, P. et al., Quetiapine in Bipolar Disorder: Increasing Evicence of Efficacy and Tolerability, Drugs of Today, vol. 40, No. 10, Oct. 2004 (Oct. 2004), p. 837, XP055068503, ISSN: 0025-7656, DOI: 10.1358/dot.2004.40.10.863744 *the whole document*.
Goodson, In Medical Applications of Controlled Release, supra, vol. 2, pp. 115-138 (1984).
Greene, T.W., "Protective Groups in Organic Synthesis," A Wiley-Interscience Publication, John Wiley & Sons, New York, 1981, pp. 218-287.
Hsien, "Multiple Lamination for Transdermal Patches," Controlled Released Systems Fabrication Technology, v. 1, pp. 167-188 (1988).
Langer, Science, 249:1527-1533 (1990).
Mahatthanatrakul et al., Int. J. Clin. Pharmacol. Ther., 46(9):489-496 (2008).
Matheson et al., Quetiapine, CNS drugs, 2000, vol. 14, pp. 157-172.
Merriam-Webster Dictionary, definition of prodrug, http://www.merriam-webster.com/medical/prodrug, accessed on Nov. 18, 2012.
Muller, Prodrug Approaches for Enhancing the bioavailability of Drugs with Low Solubility, Chem. & Biodiversity, 2009, vol. 6, pp. 2071-2083.

(Continued)

Primary Examiner — Susan T Tran
Assistant Examiner — William Craigo
(74) Attorney, Agent, or Firm — McAndrews, Held and Malloy

(57) ABSTRACT

The presently described technology provides a novel class of prodrugs of quetiapine that can be synthesized by chemically conjugating fatty acids to quetiapine. Pharmaceutical compositions and methods of synthesizing conjugates of the present technology are also provided. Methods of treating patients with the compositions of the present technology are also provided.

23 Claims, 5 Drawing Sheets

(56) References Cited

OTHER PUBLICATIONS

Pardridge, The Blood-Brain Barrier: Bottleneck in Brain Drug Development, J. Am. Soc. Exper. NeuroTherapeutics, 2005, vol. 2, p. 3-14.
Testa et al., Hydrolysis in Drug and Prodrug Metabolism, Wiley-VCH, 2004, Chapter 4, p. 96-98.
Woods, J. Clin. Psychiatry, 64(6):663-667 (2003).
International Search Report and Written Opinion in PCT/US2010/61853, dated Feb. 24, 2011.
International Search Report and Written Opinion in PCT/US2011/27658, dated Jul. 28, 2011.
Office Action in U.S. Appl. No. 13/043,764, dated Jan. 10, 2012.
Office Action in U.S. Appl. No. 13/043,764, dated Mar. 23, 2012.
IPRP in PCT/US2010/61853, dated Jul. 12, 2012.
IPRP in PCT/US2011/27658, dated Sep. 20, 2012.
Office Action in U.S. Appl. No. 13/043,764, dated Nov. 26, 2012.
Office Action in U.S. Appl. No. 13/518,981, dated Dec. 20, 2012.
Office Action in U.S. Appl. No. 12/976,546, dated Mar. 28, 2013.
Office Action in U.S. Appl. No. 13/518,981, dated Jun. 6, 2013.
Office Action in U.S. Appl. No. 13/770,462, dated Jul. 11, 2013.
Office Action in U.S. Appl. No. 13/581,496, dated Sep. 6, 2013.
Vig et al., Amino Acid Prodrugs for Oral Delivery Challenges and Opportunities, Therapeutic Delivery, 2011, vol. 2, pp. 959-962.
Vollman et al., Synthesis and Properties of a New Water Soluble Prodrug of the Adenosine A2A Receptor Antagonist MSX-2, Molecules, 2008, vol. 13, pp. 348-359.
Jensen NH, Rodriguiz RM, Caron MG, Wetsel WC, Rothman RB, Roth BL. N-desalkylquetiapine, a potent norepinephrine reuptake inhibitor and partial 5-HT1A agonist, as a putative mediator of quetiapine's antidepressant activity. Neuropsychopharmacology 2008;33:2303-2312.
Office Action in U.S. Appl. No. 13/581,496, dated Dec. 5, 2013.
Notice of Allowance in U.S. Appl. No. 13/518,981, dated Dec. 18, 2013.
Notice of Allowance in U.S. Appl. No. 13/581,496, dated Aug. 4, 2014.
Office Action in U.S. Appl. No. 14/216,342, dated Aug. 20, 2014.
Office Action in U.S. Appl. No. 14/216,342, dated Feb. 27, 2015.
Office Action in U.S. Appl. No. 14/216,342, dated May 19, 2015.
Notice of Allowance in U.S. Appl. No. 14/216,342, dated Oct. 21, 2015.
Office Action in U.S. Appl. No. 14/525,836, dated Mar. 10, 2016.
Office Action in U.S. Appl. No. 14/216,342, dated Jul. 8, 2016.
Notice of Allowance in U.S. Appl. No. 14/525,836, dated Aug. 2, 2016.
Notice of Allowance for JP 2014-095248, dated Apr. 24, 2015.
Office Action in U.S. Appl. No. 14/525,836, dated Nov. 6, 2015.

FATTY ACID CONJUGATES OF QUETIAPINE, PROCESS FOR MAKING AND USING THE SAME

RELATED APPLICATIONS

This application claims priority to and is a continuation of U.S. application Ser. No. 15/340,533 filed on Nov. 1, 2016, which is a divisional application of U.S. application Ser. No. 14/525,836, filed on Oct. 28, 2014, which is a continuation of U.S. application Ser. No. 13/581,496, filed on Oct. 4, 2012, which is a national stage entry of PCT/US2011/027658, filed on Mar. 9, 2011, which claims priority to and benefit from U.S. Provisional Application No. 61/312,977, filed on Mar. 11, 2010, the content of all of which are incorporated herein by reference in their entireties.

BACKGROUND OF THE INVENTION

Quetiapine has been used in the treatment of severe mental illness in approximately 70 countries including the US, Canada, most Western European countries, and Japan. Quetiapine is a dibenzothiazepine derivative with a relatively broad receptor binding profile. It has major affinity to cerebral serotonergic (5-$HT_{2A}$), histaminergic (H1), and dopaminergic $D_1$ and $D_2$ receptors, moderate affinity to $\alpha_1$- and $\alpha_2$-adrenergic receptors, and minor affinity to muscarinergic M1 receptors; it demonstrates a substantial selectivity for the limbic system. This receptor avidity profile with relatively higher affinity for the 5-$HT_{2A}$ receptor compared to the $D_2$ receptor is considered to be, at least in part, responsible for the antipsychotic characteristics and low incidence of extrapyramidal side-effects of quetiapine.

The efficacy of quetiapine in reducing positive and negative symptoms of schizophrenia has been proven in several clinical trials with placebo-controlled comparators. Quetiapine has also demonstrated robust efficacy for treatment of cognitive, anxious-depressive, and aggressive symptoms in schizophrenia. Quetiapine also has proven efficacy and tolerability in the treatment of moderate to severe manic episodes, and in the treatment of juveniles with oppositional-defiant or conduct disorders, and in the geriatric population with dementia. Data indicate that quetiapine is also effective in the treatment of bipolar depressive symptoms without increasing the risk of triggering manic episodes, and in borderline personality disorder. In comparison with other antipsychotics, quetiapine has a favorable side-effect profile.

In clinical trials, only small insignificant prolongations of the QT interval were observed. Weight-gain liabilities and new-onset metabolic side-effects occupy a middle-ground among newer antipsychotics. As a result of its efficacy and tolerability profile, quetiapine has become well established in the treatment of schizophrenia and other psychiatric disorders.

Recently though, in addition to large interindividual variability and weight gain, reports surfaced on treatment emergent diabetes (TED), associated with chronic administration of quetiapine. Additionally, the therapeutical dose of quetiapine is relatively high, leading to the need of making pharmaceutical compositions with relatively high concentrations of the active ingredient (up to 60%). Making tablets of such a high concentration of the active pharmaceutical ingredient (API) is difficult, particularly due to the bad tabletting properties of the API.

Therefore, an advantageous alternative would be a formulation that allows for better bioavailability of the drug, and avoids the need for repeated administration thereby helping in regimen adherence by otherwise reluctant psychiatric patients. The formulation would preferably exhibit a desired release profile that can lower the total necessary therapeutical dose and/or reduce side-effects such as TED and/or weight gain.

BRIEF SUMMARY OF THE INVENTION

The present technology is directed to a novel class of prodrugs of quetiapine that can be synthesized by chemically conjugating fatty acids to quetiapine. The chemical bond between these two moieties is established in one aspect, by reacting the primary hydroxyl functionality of quetiapine or any one of its active metabolites or non-binding electrons of its active metabolites with the carboxyl group of the fatty acids, thereby creating an ester conjugate or tertiary amide conjugate.

In one embodiment, the invention provides a composition for treating a psychiatric disorder such as schizophrenia, bipolar disorder, obsessive-compulsive disorder, post-traumatic stress disorder, restless legs syndrome, autism, alcoholism, depression, insomnia or Tourette syndrome in a subject, comprising a conjugate of 2-(2-(4-(dibenzo[b,f][1,4]thiazepin-11-yl) piperazin-1-yl)ethoxy)ethanol (quetiapine), an active metabolite or derivative thereof and at least one fatty acid such as a saturated fatty acid in one aspect, or a monounsaturated fatty acid, a polyunsaturated fatty acid, an acetylenic fatty acid, a substituted fatty acid, a heteroatom containing fatty acid, a ring containing fatty acid or a combination thereof in other discrete aspects, as well as a salt thereof, a derivative thereof, or their combination. In another embodiment, the composition is formulated for oral, sublingual, transdermal, intrathecal or suppository administration wherein quetiapine or an active metabolite thereof such as N-desalkyl-quetiapine (norquetiapine; norQTP) and a fatty acid such as valproate is present in the composition in an amount of from about 1 to about 2000 mg/dose based on equimolar weight of unconjugated quetiapine, or unconjugated active metabolite. Oral administration is carried out in certain embodiments using a tablet, capsule, caplet, pill, powder, troche, lozenge, slurry, liquid solution, suspension, emulsion, elixir or oral thin film (OTF), each a discrete embodiment of the form of oral administration.

In another embodiment, the invention provides quetiapine or any one of its active metabolites or derivatives, conjugated to at least one fatty acid as represented by any one of the structures of general formulas I-IV:

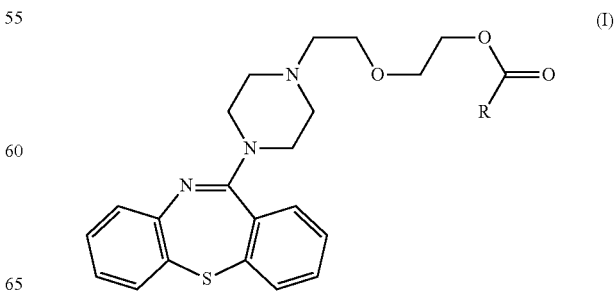

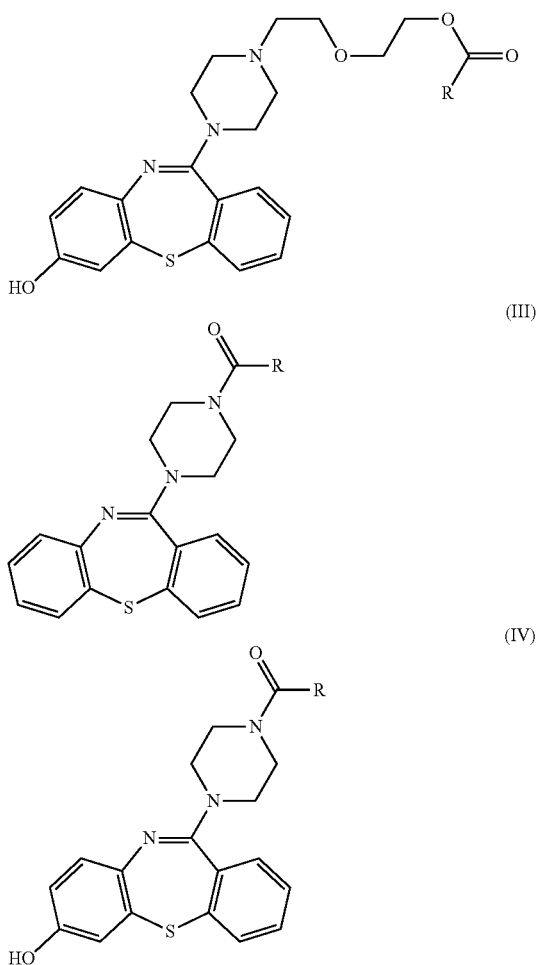

a pharmaceutically acceptable salt thereof, a derivative thereof or a combination thereof, wherein "R" is a fatty acid side-chain selected from the group consisting at least one of the fatty acids set forth in Tables I-VII.

In another embodiment, the invention provides a method of conjugating quetiapine or an active metabolite thereof such as 7-hydroxy-quetiapine (7-OH-QTP) and at least one fatty acid such as a saturated fatty acid, a monounsaturated fatty acid, a polyunsaturated fatty acid such as docosahexaenoic acid (DHA) or eicosapentaenoic acid (EPA), an acetylenic fatty acid, a substituted fatty acid, a heteroatom containing fatty acid, a ring containing fatty acid or a combination thereof, comprising the steps of: in the presence of a base such as 4-methylmorpholine (NMM) or 4-(dimethylamino)pyridine (DMAP), attaching a fatty acid wherein the fatty acid has an optionally protected functional moiety therein, to quetiapine or its active metabolite whereby the functionalized fatty acid is protected with tert-butyloxycarbonyl (Boc) in one embodiment; followed by deprotecting the functionalized moiety on the fatty acid, thereby conjugating quetiapine or an active metabolite thereof and at least one fatty acid.

In one embodiment, the invention provides a method of increasing the relative bioavailability of quetiapine or an active metabolite thereof such as norQTP or 7-OH-QTP, comprising the step of conjugating quetiapine or its active metabolite to at least one fatty acid such as a saturated fatty acid such as valproic acid, a monounsaturated fatty acid such as palmitoleic acid, a polyunsaturated fatty acid such as DHA or EPA, or a combination thereof, thereby modulating the hydrophobicity, solubility, improving absorption, altering metabolic pathways or their combination of the conjugated quetiapine or the active metabolite thereof, resulting in certain embodiments, in a higher maximum observed blood plasma concentration ($C_{max}$) and/or area under the curve (AUC) and/or longer or similar amount of time after administration at which $C_{max}$ occurs ($T_{max}$) values compared to those produced by unconjugated quetiapine when administered at equimolar doses. Increased bioavailability may also result in: reduced interindividual variability in one embodiment; decreased number and/or amount of active, inactive, toxic or non-toxic metabolites; increased number and/or amount of active metabolites produced by unconjugated quetiapine or its active metabolite in other discrete embodiments of the outcome of increased bioavailability resulting from the conjugation of quetiapine or the active metabolite and at least one fatty acid.

In another embodiment, the invention provides a method of treating a psychiatric disorder requiring the binding of dopamine receptor(s), serotonin receptor(s), or histamine receptor(s) or a combination or permutation thereof in a subject such as human or mammal, comprising the step of orally, intrathecally transdermally or rectally administering to the subject a composition comprising a therapeutically effective amount of about 1-2000 mg/dose based on equimolar weight of unconjugated API of quetiapine or an active metabolite thereof such as 7-hydroxy-N-desalkyl-quetiapine, conjugated to at least one fatty acid such as a saturated fatty acid, a monounsaturated fatty acid, a polyunsaturated fatty acid, an acetylenic fatty acid, a substituted fatty acid, a heteroatom containing fatty acid such as colneleic acid, a ring containing fatty such as ladderane-butanoic acid or a combination thereof, a pharmaceutically acceptable salt or derivative thereof, thereby binding a dopamine receptor, a serotonin receptor, histamine receptor or any permutation combination thereof. In one embodiment, the invention provides a method of treating schizophrenia or bipolar disorder in a subject in need thereof, comprising the step of administering to the subject a composition comprising a therapeutically effective amount of quetiapine or an active metabolite thereof, conjugated to at least one fatty acid such as 7-hydroxy-N-desalkyl-quetiapinyl-octanoate, or 7-hydroxy-quetiapinyl-valproate, a pharmaceutically acceptable salt, or derivative thereof, thereby binding to a dopamine receptor, a serotonin receptor, or both and treating schizophrenia or bipolar disorder.

In one embodiment, the invention provides a quetiapine conjugate transdermal therapeutic system, comprising a quetiapine conjugate reservoir comprised essentially of a) a gelling agent that is selected from the group consisting of carbomer, carboxyethylene, polyacrylic acid, cellulose derivatives, ethyl cellulose, hydroxypropyl methyl cellulose, ethyl hydroxyethyl cellulose, carboxymethyl cellulose, hydroxypropyl cellulose, hydroxyethyl cellulose, natural gums, arabic, xanthan, guar gums, alginates, polyvinylpyrrolidone derivatives, polyoxyethylene polyoxypropylene copolymers, chitosan, polyvinyl alcohol, pectin, or veegum; and b) quetiapine, an active metabolite or derivative thereof and therapeutically acceptable salts thereof, and mixtures thereof; conjugated to at least one of a fatty acid described herein that functions as permeation enhancer. In one embodiment, the fatty acid functioning as permeation enhancer is a short-chain fatty acid (SCFA) such as butyric acid, a medium-chain fatty acid (MCFA) such as caprylic acid, a long-chain fatty acid (LCFA) such as oleic acid, or a combination thereof. In another embodiment, the fatty acid functioning as permeation enhancer is a saturated fatty acid, a monounsaturated fatty acid, a polyunsaturated fatty acid, an acetylenic fatty acid, a substituted fatty acid, a heteroatom containing fatty acid, or a ring containing fatty acid, or a combination thereof. In another embodiment, the fatty acid functioning as permeation enhancer is a fatty acid functionalized to be cross-linked to at least one other functionalized fatty acid which is optionally conjugated to quetiapine, an active metabolite or derivative thereof, or their combination. In another embodiment, the cross-linked fatty acids, at least some of which are conjugated to quetiapine, an active metabolite or derivative thereof, or their combination, form a polymeric gel. In another aspect, the cross-linked fatty acid is a polyunsaturated fatty acid such as α-linolenic acid, a polyhydroxy fatty acid, and epoxy containing fatty acid or their combination. In one embodiment, the transdermal system further comprises a non-permeable backing and a permeable membrane located between the release matrix and a site of interest on the skin of a subject in the form of a transdermal patch with an impermeable cover layer and removable protection layer, wherein the conjugate of quetiapine or an active metabolite and/or an active derivative thereof and at least one of a saturated fatty acid, a monounsaturated fatty acid, a polyunsaturated fatty acid, an acetylenic fatty acid, a heteroatom containing fatty acid, a ring containing fatty acid, a cross-linked fatty acid, a salt thereof, a derivative thereof or their combination is present in an amount that produces plasma concentrations of quetiapine, its active metabolite and/or active derivative thereof between about 89% and about 115% of the plasma concentrations achieved after oral administration of an amount of between about 1 mg and about 3000 mg per unit dose.

In another embodiment, the invention provides for the use of a therapeutically effective amount of a conjugate of quetiapine, its active metabolite and/or active derivative and/or their combination; and a saturated fatty acid such as valproic acid, a monounsaturated fatty acid, a polyunsaturated fatty acid, an acetylenic fatty acid, a heteroatom containing fatty acid, a ring containing fatty acid, a cross-linked fatty acid or a combination thereof; in a medicament for the treatment of a disorder associated with serotonin, dopamine or histamine dysfunction in a subject in need thereof.

BRIEF DESCRIPTION OF THE DRAWINGS

The invention will be better understood from a reading of the following detailed description taken in conjunction with the figures and examples in which like reference designators are used to designate like elements or findings, and in which.

DETAILED DESCRIPTION OF THE INVENTION

Figure 1:
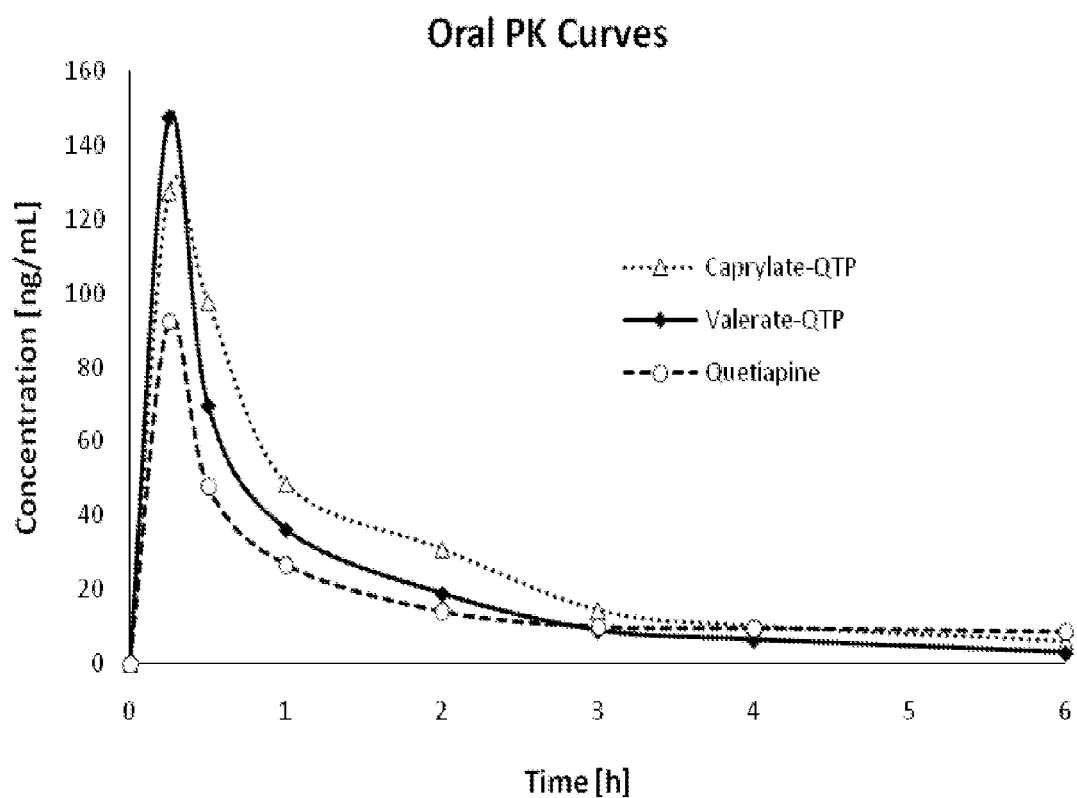
FIG. 1 shows an oral PK rat study comparing plasma concentrations of quetiapine produced by unconjugated quetiapine and by the valeric acid (valerate-QTP) and caprylic acid (caprylate-QTP) conjugates.
Figure 2:
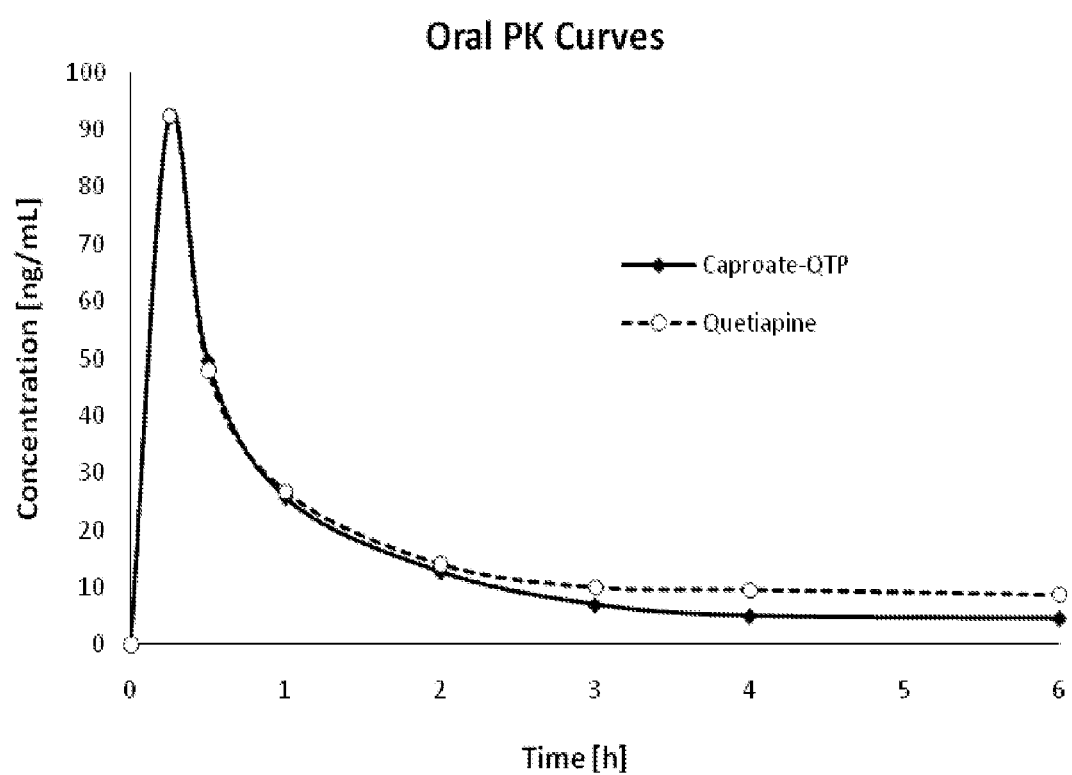
FIG. 2 shows an oral PK rat study comparing plasma concentrations of quetiapine produced by unconjugated quetiapine and by the caproic acid conjugate (caproate-QTP)
Figure 3:
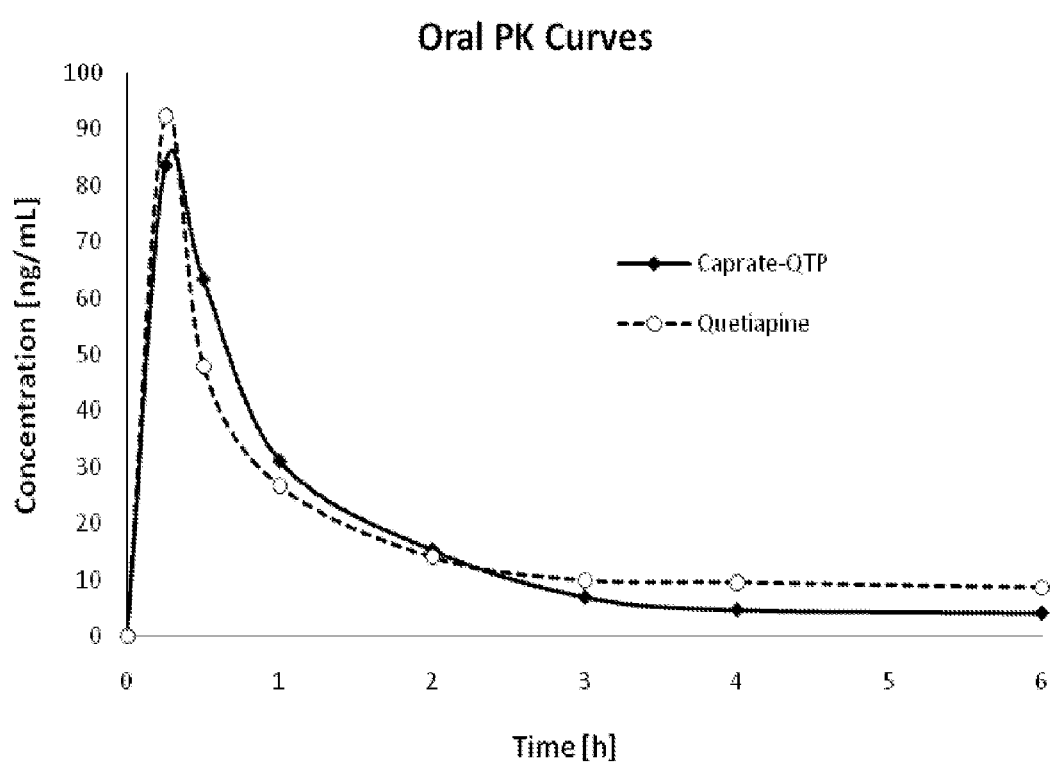
FIG. 3 shows oral PK rat study comparing plasma concentrations of quetiapine produced by unconjugated quetiapine and by the capric acid conjugate (caprate-QTP)
Figure 4:
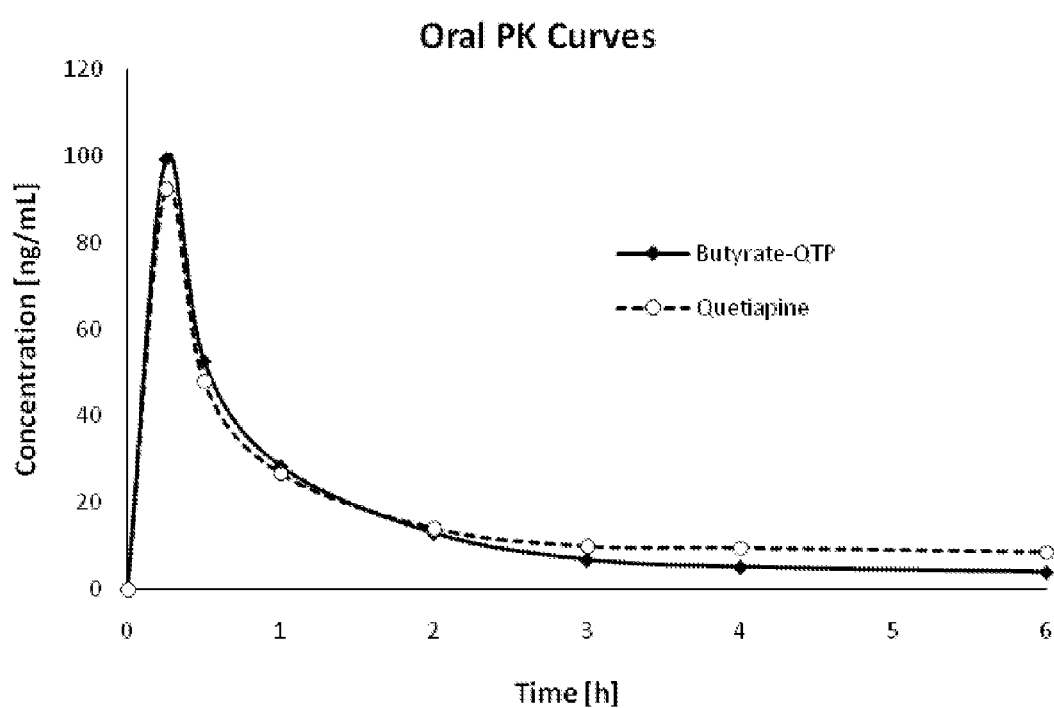
FIG. 4 shows oral PK rat study comparing plasma concentrations of quetiapine produced by unconjugated quetiapine and by the butyric acid conjugate (butyrate-QTP)

In one embodiment, the invention is directed to quetiapine conjugate compositions, their synthesis and use. In another embodiment, the invention is directed to quetiapine conjugates with saturated, monounsaturated, polyunsaturated, acetylenic, substituted, heteroatom containing, ring containing fatty acids or their combination, their syntheses and use in therapeutic compositions for the treatment of psychiatric disorders.

Quetiapine:

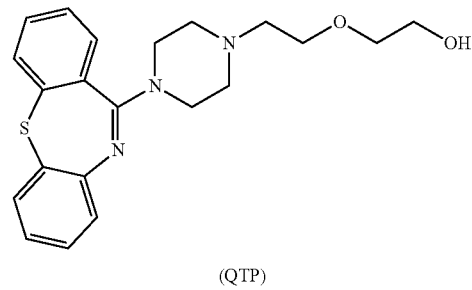 [SMILES: OCCOCCN1CCN(C2=Nc3ccccc3Sc3ccccc32)CC1]

(QTP)

is an atypical antipsychotic in the sub-class of multi-acting receptor-targeted antipsychotics (MARTA). As such, it exhibits antagonist activity at the dopamine $D_2$ and $D_1$ receptors, the serotonin $5\text{-}HT_2$ and $5\text{-}HT_{1A}$ receptors, the adrenergic $\alpha_1$ and $\alpha_2$ receptors and the histamine $H_1$ receptor. While the modulation of the dopamine and serotonin receptors are thought to be responsible for the therapeutic activity of quetiapine, the affinity of quetiapine to the histamine and adrenergic receptors may cause of some of its side-effects, particularly its somnolent and hypotensive effects.

Quetiapine is currently approved for the following indications:

Acute and maintenance treatment of schizophrenia.

Acute depressive episodes associated with bipolar disorder.

Acute manic or mixed episodes associated with bipolar I disorder as monotherapy and as an adjunct to lithium or divalproex therapy.

Maintenance treatment of bipolar I disorder as adjunct therapy to lithium or divalproex.

Quetiapine has also shown acceptable efficacy in some off-label indications that include obsessive-compulsive disorder, post-traumatic stress disorder, restless legs syndrome, autism, alcoholism, depression and Tourette syndrome. It has been used as sedative for patients with sleep or anxiety disorders.

In one embodiment, the compositions comprising the prodrugs provided herein may be administered for the treatment of schizophrenia or bipolar disorder or for any condition that may require the blocking of dopamine or serotonin receptors.

The term "prodrug", as used herein, refers in one embodiment to a metabolic precursor of a compound of the conjugated quetiapine provided herein, which is pharmaceutically acceptable. A prodrug may be inactive when administered to a subject but is converted in vivo to an active compound. In one embodiment, the term "active metabolite", refers to a metabolic product of quetiapine that is pharmaceutically acceptable and effective. In another embodiment, the term "active metabolite" refers to a metabolic product of quetiapine that is effective for ameliorating, treating or preventing schizophrenia, bipolar disorder, obsessive-compulsive disorder, post-traumatic stress disorder, restless legs syndrome, autism, alcoholism, depression, insomnia or Tourette syndrome.

Prodrugs are often useful because, in some embodiments, they may be easier to administer or process than the parent drug. They may, for instance, be bioavailable by oral administration whereas the parent is not. The prodrug may also have improved solubility in pharmaceutical compositions over the parent drug. An embodiment of a prodrug would be a short-chain fatty acid, such as butyric acid bonded to a primary hydroxyl group of quetiapine where the short chain fatty acid is metabolized to reveal the active moiety. In certain embodiments, upon in vivo administration, a prodrug is hydrolytically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolic stability or the transport characteristics of a drug in certain embodiments, to mask, ameliorate or reduce side-effects or toxicity, to improve the flavor of a drug or to alter other characteristics or properties of a drug.

In another embodiment, the term "active metabolite" refers to a biologically active derivative of a compound that is formed when the compound is metabolized. The term "metabolized," refers in one embodiment to the sum of the processes (including, but not limited to, hydrolysis reactions and reactions catalyzed by enzymes, such as, oxidation reactions, de-esterification reactions and/or proteolysis reactions) by which a particular substance is changed by an organism. Thus, enzymes may produce specific structural alterations to a compound. In one embodiment, cytochrome P450 (CYP) catalyzes a variety of oxidative and reductive reactions while some isoforms, such as CYP3A4 are involved in de-esterification. Further information on metabolism may be obtained from The Pharmacological Basis of Therapeutics, 9th Edition, McGraw-Hill (1996), incorporated herein by reference in its entirety. Metabolites of the compounds disclosed herein can be identified either by administration of compounds to a host under conditions allowing for the determination of activity by the metabolite and analysis of tissue samples from the host, or by incubation of compounds with hepatic cells in vitro and analysis of the resulting compounds. In some embodiments, a compound is metabolized to pharmacologically active metabolites.

In another embodiment, fatty acids conjugated to quetiapine create ester prodrugs that can release the active antipsychotic. The prodrugs provided herein, alter the pharmacology, pharmacokinetics and/or metabolism of quetiapine. As a result; by choosing suitable fatty acids, the bioavailability of quetiapine is increased. In one embodiment, the side-effect profile and inter-individual variability in plasma concentrations of the active are improved or reduced.

In one embodiment, provided herein is a novel class of prodrugs of quetiapine, which is synthesized by chemically conjugating fatty acids to quetiapine. The chemical bond between these two moieties is established by reacting the primary hydroxyl functionality of quetiapine with the carboxyl group of the fatty acids, thereby creating an ester conjugate. In another embodiment, the fatty acids in the context of prodrugs described herein are also referred to as "ligands" that are attached to the parent molecule (i.e., quetiapine).

In one embodiment, the conjugates of quetiapine, its active metabolite and/or active derivative and/or their combination; and a saturated fatty acid such as valproic acid, a monounsaturated fatty acid, a polyunsaturated fatty acid, an acetylenic fatty acid, a heteroatom containing fatty acid, a ring containing fatty acid or a combination thereof, creates a new class of drugs where both parent and ligand are active pharmaceutical ingredients (API) and their conjugation creates a synergistic effect in their efficacy, reduced adverse side-effects and the like.

Accordingly and in another embodiment, provided herein is a composition for treating a psychiatric disorder in a subject, comprising a conjugate of 2-(2-(4-(dibenzo[b,f][1, 4]thiazepin-11-yl)piperazin-1-yl)ethoxy)ethanol (quetiapine), an active metabolite or derivative thereof and at least one fatty acid, a salt thereof, a derivative thereof or a combination thereof.

In one embodiment, the fatty acids used in conjunction with the compositions, methods and systems described herein encompass fatty acids of the broadest definition such as any that are natural and synthetic, short and long chain, saturated and unsaturated, straight chain and branched, containing a ring or not, substituted and non-substituted fatty acids. In another embodiment, the fatty acids of this invention may or may not include heteroatoms and keto groups.

Depending on the fatty acids conjugated to quetiapine, the prodrug formed can be either neutral, free acid, free base or pharmaceutically acceptable anionic or cationic salt forms or salt mixtures with any ratio between positive and negative components. These salt forms include, but are not limited to: acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsufate, 2-napsylate, nicotinate, nitrate, orotate, stearate, tosylate, thiocyanate, acefyllinate, aceturate, fattysalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate.

In the compositions and methods described herein, the synthesized prodrugs are designed to breakdown enzymatically, through hydrolysis or otherwise in vivo to quetiapine and the respective fatty acids or their metabolites. The fatty acids are preferably considered Generally Regarded As Safe (GRAS) or non-toxic at the released concentrations.

Without limiting the scope of this invention, examples of fatty acids include common natural saturated fatty acids of the general formula $C_nH_{2n+1}COOH$ and a chain length of $C_4$ to $C_{30}$. In another embodiment fatty acids conjugated to quetiapine have short to medium chain lengths of $C_2$ to $C_8$. Other embodiments include naturally occurring omega-3 and omega-6 unsaturated fatty acids.

Fatty Acids

Although this invention is not limited to naturally occurring fatty acids, in one embodiment, the term "fatty acids" refer to carboxylic acids that are related to or are found in their esterified form in plants and animals. While many naturally occurring fatty acids contain an even number of carbons, the fatty acids described herein encompass any chain lengths with an odd or even number of carbons.

Definitions $\mathbb{R}$ is defined as a multi-set of residues whose members can be any of the substituents listed in the tables provided herein. $\mathbb{R}$ is a multiset, i.e., it can include multiple identical elements which are in this case chemical substituents (e.g., two methyl groups).

The parameters m and m' with $m=|\mathbb{R}|$ and $m'|\mathbb{R}'|$ are the cardinalities of the specific multisets $\mathbb{R}$ and $\mathbb{R}'$ and thus describe the number of elements in $\mathbb{R}$ and $\mathbb{R}'$.

The parameters a, m, m', n, n', p, q, x, x', y, y' are integers. p describes the number of double bonds and q the number of triple bonds in a given carbon chain.

Classes of Fatty Acids

Straight/Branched Chain Fatty Acids:

General formula: $C_nH_{2(n-p-2q)-m+1}\mathbb{R}\text{-}CO_2H$ $n\geq 2q+p+1, p\geq 0, q\geq 1, 2(n-p-2q)+1\geq m=|\mathbb{R}|\geq 1$ Carbon Chain without Substituent ($\mathbb{R}=\{H\}$):

General formula: $C_nH_{2(n-p-2q)+1}\mathbb{R}\text{-}CO_2H$ $n\geq 2q+p+1, p\geq 0, q\geq 0$ Saturated Fatty Acids:

General formula: $C_nH_{2n+1}\text{—}CO_2H$ $n\geq 1$

Monounsaturated Fatty Acids (Cis or Trans):

General formula: $C_nH_{2n-1}\text{—}CO_2H$ $n\geq 2$

Polyunsaturated Fatty Acids (any Cis/Trans):

General formula: $C_nH_{2(n-p)+1}\text{—}CO_2H$ $n\geq p+1, p\geq 2$

Acetylenic Fatty Acids (any Cis/Trans):

General formula: $C_nH_{2(n-p-2q)+1}\text{—}CO_2H$ $n\geq 2q+p+1, p\geq 0, q\geq 1$ Carbon Chain with Substituent(s) ($\mathbb{R}\neq\{H\}$):

General formula: $C_nH_{2(n-p-2q)-m+1}\mathbb{R}\text{—}CO_2H$ $n\geq 2q+p+1, p\geq 0, q\geq 1, 2(n-p-2q)+1\geq m=|\mathbb{R}|\geq 1$ Alkyl group: alkyl$\in\mathbb{R}$
Hydroxyl group: OH$\in\mathbb{R}$
Carboxyl group: $CO_2H\in\mathbb{R}$
Sulfate group: $SO_4H\in\mathbb{R}$
Methoxy group: $OCH_3\in\mathbb{R}$
Acetoxy group: $OCOCH_3\in\mathbb{R}$
Aldehyde group: CHO$\in\mathbb{R}$
Halogens: any of F, Cl, Br, I$\in\mathbb{R}$
Nitro group: $NO_2\in\mathbb{R}$ Carbon Chain with Divinyl Ether Function:

General formula: $\mathbb{R}H_{2(n-p-2q)-m+1}C_n\text{—CH=CH—}$
$\text{O—CH=CH—}C_{n'}H_{2(n'-p'-2q')-m'}\mathbb{R}'\text{—}CO_2H$ $n\geq 2q+p+1, p\geq 0, q\geq 0, n'\geq 2q'+p'+1, p'\geq 0, q'\geq 0, 2(n-p-2q)+1\geq m=|\mathbb{R}|\geq 1,$ $2(n'-p'-2q)+1\geq m'=|\mathbb{R}'|\geq 1$ Carbon Chain Containing Sulfur:

General formula: $\mathbb{R}H_{2(n-p-2q)-m+1}C_n\text{—S—}C_{n'}$
$H_{2(n'-p'-2q')-m'}\mathbb{R}\text{—}CO_2H$ $n\geq 2q+p+1, p\geq 0, q\geq 0, n'\geq 2q+p'+1, p'\geq 0, q'\geq 0,$
$2(n-p-2q)+1\geq m=|\mathbb{R}|\geq 1,$ $2(n'-p'-2q)+1\geq m'=|\mathbb{R}'|\geq 1$ Carbon Chain with Keto Group:

General formula: $\mathbb{R}H_{2(n-p-2q)-m+1}C_n\text{—CO—}C_{n'}$
$H_{2(n'-p'-2q')-m'}\mathbb{R}\text{—}CO_2H$ $n\geq 2q+p+1, p\geq 0, q\geq 0, n'\geq 2q+p'+1, p'\geq 0, q'\geq 0, 2(n-p-2q)+1\geq m=|\mathbb{R}|\geq 1,$ $2(n'-p'-2q)+1\geq m'=|\mathbb{R}'|\geq 1$ Ring Containing Fatty Acids:
Cyclopropane Ring:
General Formula:

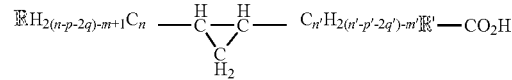

$n\geq 2q+p+1, p\geq 0, q\geq 0, n'\geq 2q'+p'+1, p'\geq 0, q'\geq 0, 2(n-p-2q)+1\geq m=|\mathbb{R}|\geq 1,$ $2(n'-p'-2q)+1\geq m'=|\mathbb{R}'|\geq 1$ Cyclopropene Ring:
General Formula:

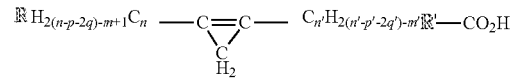

$n\geq 2q+p+1, p\geq 0, q\geq 0, n'\geq 2q'+p'+1, p'\geq 0, q'\geq 0, 2(n-p-2q)+1\geq m=|\mathbb{R}|\geq 1,$ $2(n'-p'-2q)+1\geq m'=|\mathbb{R}'|\geq 1$ Epoxy Ring:
General Formula:

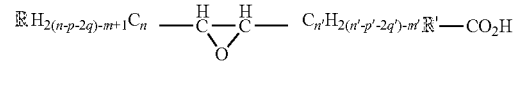

$n\geq 2q+p+1, p\geq 0, q\geq 0, n'\geq 2q'+p'+1, p'\geq 0, q'\geq 0, 2(n-p-2q)+1\geq m=|\mathbb{R}|\geq 1,$ $2(n'-p'-2q)+1\geq m'=|\mathbb{R}'|\geq 1$ Ladderanes:
General Formula:

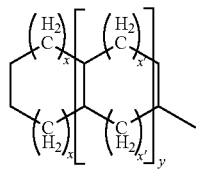 

$n \geq 2q+p+1, p \geq 0, q \geq 1, 2(n-p-2q)+$
$1 \geq m = |\mathbb{R}| \geq 1; x, x', y, y' = 1 \text{ or } 0$ 5- and 6-Membered Rings:

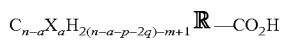

$a \geq 1, n \geq a+2q+p+1, p \geq 0, q \geq 1, 2(n-a-p-2q)+1 \geq m = |\mathbb{R}| \geq 1$ cyclopentyl/cyclopentenyl rings: X=

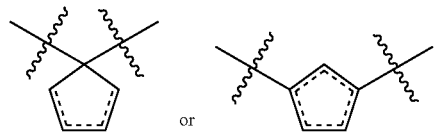

cyclohexyl/cyclohexenyl rings: X=

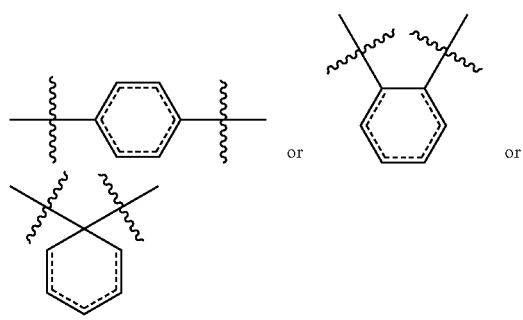

The broken line indicates the presence of a single or double bond.

Furan Ring:

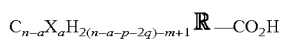

$a \geq 1, n \geq a+2q+p+1, p \geq 0, q \geq 1, 2(n-a-p-2q)+1 \geq m = |\mathbb{R}| \geq 1$

X=

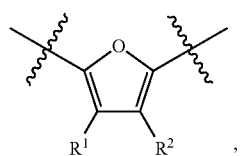

$R^1, R^2 = H, CH_3$ or $CO_2H$

Examples of Fatty Acids

Without limiting the scope of this invention, provided herein are embodiments of fatty acids that can be attached to quetiapine via an ester bond to form new prodrug entities.

In the following embodiments "shorthand designation" is an abbreviated formula to describe the structure of fatty acids. The terminus of this formula (after the "-") indicates the number of carbons in the n-carboxylic acid chain followed by the number of double bonds (in the format c:d). Substituents on the core carbon chain are expressed by a number and a letter code in ascending numerical order at the beginning of the formula. The number indicates the position of the substituent on the n-carbon chain (numbering starts with the carboxyl group) and the letter code the type of substituent.

The definitions of the letter codes are: c=cis, t=trans, e=double bond with undefined stereochemistry, y=triple bond, m=methyl, h=hydroxyl, dioic=dicarboxylic acid, Md=methylidene, a=alkyl, Sul=sulfate, OMe=methoxy, OAc=acetoxy, o=oxo, F=fluoro, Cl=chloro, Br=bromo, Nitro=nitro, k=keto; bridging atoms forming 3-membered rings within the n-carbon chain are shown as: X-Yepoxy=oxygen bridging carbons at position X and Y, X-YM=methylene bridging saturated carbons at position X and Y (cyclopropyl), X-Ye=methylene bridging unsaturated carbons at position X and Y (cyclopropenyl).

At the end of the formula (in parentheses) the position of the first double bond is shown starting from the ω-carbon of the n-carboxylic acid (in the format n-d).

TABLE I

| Saturated fatty acids | | |
| --- | --- | --- |
| Systematic name | Trivial name | Formula |
| methanoic | formic | $HCO_2H$ |
| ethanoic acid | acetic | $CH_3CO_2H$ |
| propanoic acid | propionic | $CH_3CH_2CO_2H$ |
| butanoic | butyric | $CH_3(CH_2)_2CO_2H$ |
| pentanoic | valeric | $CH_3(CH_2)_3CO_2H$ |
| hexanoic | caproic | $CH_3(CH_2)_4CO_2H$ |
| heptanoic | enanthic | $CH_3(CH_2)_5CO_2H$ |
| octanoic | caprylic | $CH_3(CH_2)_6CO_2H$ |
| 2-propylpentanoic acid | valproic | $(CH_3((CH_2)_2))_2CHCO_2H$ |
| nonanoic | pelargonic | $CH_3(CH_2)_7CO_2H$ |
| decanoic | capric | $CH_3(CH_2)_8CO_2H$ |
| dodecanoic | lauric | $CH_3(CH_2)_{10}CO_2H$ |
| tetradecanoic | myristic | $CH_3(CH_2)_{12}CO_2H$ |
| hexadecanoic | palmitic | $CH_3(CH_2)_{14}CO_2H$ |
| heptadecanoic | margaric (daturic) | $CH_3(CH_2)_{15}CO_2H$ |
| octadecanoic | stearic | $CH_3(CH_2)_{16}CO_2H$ |
| eicosanoic | arachidic | $CH_3(CH_2)_{18}CO_2H$ |
| docosanoic | behenic | $CH_3(CH_2)_{20}CO_2H$ |
| tetracosanoic | lignoceric | $CH_3(CH_2)_{22}CO_2H$ |
| hexacosanoic | cerotic | $CH_3(CH_2)_{24}CO_2H$ |
| heptacosanoic | carboceric | $CH_3(CH_2)_{25}CO_2H$ |
| octacosanoic | montanic | $CH_3(CH_2)_{26}CO_2H$ |
| triacontanoic | melissic | $CH_3(CH_2)_{28}CO_2H$ |
| dotriacontanoic | lacceroic | $CH_3(CH_2)_{30}CO_2H$ |
| tritriacontanoic | ceromelissic (psyllic) | $CH_3(CH_2)_{31}CO_2H$ |
| tetratriacontanoic | geddic | $CH_3(CH_2)_{32}CO_2H$ |
| pentatriacontanoic | ceroplastic | $CH_3(CH_2)_{33}CO_2H$ |

TABLE II

Monounsaturated fatty acids

| Systematic name | Trivial name | Shorthand designation | Formula |
|---|---|---|---|
| 4-decenoic | obtusilic | 4c-10:1 (n-6) | $CH_3(CH_2)_4C=C(CH_2)_2CO_2H$ |
| 9-decenoic | caproleic | 9c-10:1 (n-1) | $HC=CH(CH_2)_7CO_2H$ |
| 5-lauroleic | lauroleic | 5c-12:1 (n-7) | $CH_3(CH_2)_5CH=CH(CH_2)_3CO_2H$ |
| 4-dodecenoic | linderic | 4c-12:1 (n-8) | $CH_3(CH_2)_6CH=CH(CH_2)_2CO_2H$ |
| 9-tetradecenoic | myristoleic | 9c-14:1 (n-5) | $CH_3(CH_2)_3CH=CH(CH_2)_7CO_2H$ |
| 5-tetradecenoic | physeteric | 5c-14:1 (n-9) | $CH_3(CH_2)_7CH=CH(CH_2)_3CO_2H$ |
| 4-tetradecenoic | tsuzuic | 4c-14:1 (n-10) | $CH_3(CH_2)_8CH=CH(CH_2)_2CO_2H$ |
| 9-hexadecenoic | palmitoleic | 9c-16:1 (n-7) | $CH_3(CH_2)_5CH=CH(CH_2)_7CO_2H$ |
| 6-hexadecenoic | sapienic | 6c-16:1 (n-10) | $CH_3(CH_2)_8CH=CH(CH_2)_4CO_2H$ |
| 6-octadecenoic | petroselinic | 6c-18:1 (n-12) | $CH_3(CH_2)_{10}CH=CH(CH_2)_4CO_2H$ |
| 9-octadecenoic | oleic | 9c-18:1 (n-9) | $CH_3(CH_2)_7CH=CH(CH_2)_7CO_2H$ |
| 9-octadecenoic | elaidic | 9t-18:1 (n-9) | $CH_3(CH_2)_7CH=CH(CH_2)_7CO_2H$ |
| 11-octadecenoic | vaccenic (asclepic) | 11c-18:1 (n-7) | $CH_3(CH_2)_5CH=CH(CH_2)_9CO_2H$ |
| 9-eicosenoic | gadoleic | 9c-20:1 (n-11) | $CH_3(CH_2)_9CH=CH(CH_2)_7CO_2H$ |
| 11-eicosenoic | gondoic | 11c-20:1 (n-9) | $CH_3(CH_2)_7CH=CH(CH_2)_9CO_2H$ |
| 11-docosenoic | cetoleic | 11c-22:1 (n-11) | $CH_3(CH_2)_9CH=CH(CH_2)_9CO_2H$ |
| 13-docosenoic | erucic | 13c-22:1 (n-9) | $CH_3(CH_2)_7CH=CH(CH_2)_{11}CO_2H$ |
| 15-tetracosenoic | nervonic | 15c-24:1 (n-9) | $CH_3(CH_2)_7CH=CH(CH_2)_{13}CO_2H$ |

TABLE III

Polyunsaturated fatty acids

| Systematic Name | Trivial Name | Shorthand Designation |
|---|---|---|
| *Omega-3 Fatty Acids* | | |
| 7,10,13-hexadecatrienoic | — | 7c10c13c-16:3 (n-3) |
| octadecatrienoic | α-linolenic (ALA) | 9c12c15c-18:3 (n-3) |
| octadecatrienoic | elaidolinolenic | 9t12t15t-18:3 (n-3) |
| octadecatetraenoic | stearidonic (STD) | 6c9c12c15c-18:4 (n-3) |
| eicosatrienoic | ETE | 11c14c17c-20:3 (n-3) |
| eicosatetraenoic | ETA | 8c11c14c17c-20:4 (n-3) |
| eicosapentaenoic | timnodonic (EPA) | 5c8c11c14c17c-20:5 (n-3) |
| docosapentaenoic | clupanodonic (DPA) | 7c10c13c16c19c-22:5 (n-3) |
| docosahexaenoic | cervonic (DHA) | 4c7c10c13c16c19c-22:6 (n-3) |
| 9,12,15,18,21-tetracosapentaenoic | — | 9c12c15c18c21c-24:5 (n-3) |
| tetracosahexaenoic | nisinic | 6c9c12c15c18c21c-24:6 (n-3) |
| *Omega-6 Fatty Acids* | | |
| octadecadienoic | linoleic | 9c12c-18:2 (n-6) |
| octadecatrienoic | γ-linolenic (GLA) | 6c9c12c-18:3 (n-6) |
| 11,14-eicosadienoic | — | 11c14c-20:2 (n-6) |
| eicosatrienoic | dihomo-γ-linolenic (DGLA) | 8c11c14c-20:3 (n-6) |
| eicosatetraenoic | arachidonic (AA) | 5c8c11c14c-20:4 (n-6) |
| 13,16-docosadienoic | — | 13c16c-22:2 (n-6) |
| docosatetraenoic | adrenic | 7c10c13c16c-22:4 (n-6) |
| docosapentaenoic | osbond | 4c7c10c13c16c-22:5 (n-6) |
| *Omega-9 Fatty Acids* | | |
| eicosatrienoic | mead acid | 5c8c11c-20:3 (n-9) |
| *Conjugate Linoleic Acids (CLA)* | | |
| octadecadienoic | rumenic | 9c11t-18:2 (n-7) |
| octadecadienoic | CLA | 10t12c-18:2 (n-6) |
| *Conjugated Linolenic Acids* | | |
| octadecatrienoic | α-calendic | 8t10t12c-18:3 (n-6) |
| octadecatrienoic | β-calendic | 8t10t12t-18:3 (n-6) |
| octadecatrienoic | jacaric | 8t10t12c-18:3 (n-6) |
| octadecatrienoic | α-eleostearic | 9c11t13t-18:3 (n-5) |
| octadecatrienoic | β-eleostearic | 9t11t13t-18:3 (n-5) |
| octadecatrienoic | catalpic | 9c11t13c-18:3 (n-5) |
| octadecatrienoic | punicic | 9c11t13c-18:3 (n-5) |
| *Other Conjugated Polyenoic Fatty Acids* | | |
| octadecatrienoic | rumelenic | 9t11c16t-18:3 (n-3) |
| octadecatetraenoic | α-parinaric | 9t11t13c15t-18:4 (n-3) |
| octadecatetraenoic | β-parinaric | 9t11t13t15t-18:4 (n-3) |
| eicosapentaenoic | bosseopentaenoic | 5c8c10t12t14c-20:5 (n-6) |
| octadecadienoic | laballenic | 5e6e-18:2 (n-12) |

TABLE IV

Acetylenic fatty acids

| Systematic Name | Trivial Name | Shorthand Designation |
|---|---|---|
| *Monoacetylenic Fatty Acids* | | |
| octadecynoic | stearolic | 9y-18:0 |
| octadecynoic | tariric | 6y-18:0 |
| octadecenynoic | santalbic | 9y11t-18:1 (n-7) |
| 6,9-octadecenynoic | — | 6e9y-18:1 (n-12) |
| heptadecenynoic | pyrulic | 8y10t-17:1 (n-7) |
| octadecynoic | crepenynic | 9c12y-18:1 (n-8) |
| heptadecenynoic | scleropyric | 12y16e-17:1 (n-1) |
| *Polyacetylenic Fatty Acids* | | |
| tridecatetraenediynoic | mycomycin | 3e5e7e8e10y12y-13:4 (n-5) |
| tridecadienetriynoic | isomycomycin | 3e5e7y9y11y-13:2 (n-8) |
| octadecadienediynoic | dihydro-oropheic | 9y11y13e17e-18:2 (n-1) |
| heptadecadienediynoic | phomallenic acid B | 8e9e11y13y-17:2 (n-8) |
| octadecadienediynoic | phomallenic acid C | 9e10e12y14y-18:2 (n-8) |
| octadecenediynoic | exocarpic | 9y11y13e-18:1 (n-5) |
| octadecenetriynoic | oropheic | 9y11y13y17e-18:1 (n-1) |

TABLE V

Substituted fatty acids

| Systematic Name | Trivial Name | Shorthand Designation |
|---|---|---|
| Alkyl-Substituted Fatty Acids | | |
| methylpropanoic | isoutyric | 2m-4:0 |
| methylhexadecanoic | anteisoheptadecanoic | 14m-16:0 |
| 8-methyl-6-nonenoic | — | 6t8m-9:1 (n-3) |
| methyloctadecanoic | tuberculostearic | 10m-18:0 |
| methyloctadecanoic | anteisononadecanoic | 16m-18:0 |
| trimethyloctacosanoic | mycoceranic | 2m4m6m-28:0 |
| trimethyltetracosenoic | mycolipenic | 2m2t4m6m-24:1 (n-22) |
| heptamethyltriacontanoic | phthioceranic | 2m4m6m8m10m12m14-30:0 |
| tetramethylhexadecanoic | phytanic | 3m7m11m15m-16:0 |
| tetramethylpentadecanoic | pristanic | 2m6m10m14m-15:0 |
| Hydroxy-Substituted Fatty Acids | | |
| Monohydroxy Fatty Acids | | |
| hydroxyoctadecatrienoic | 2-hydroxylinolenic | 2h9c12c15c-18:3 (n-3) |
| hydroxyoctadecenoic | 2-hydroxyoleic | 2h9c-18:1 (n-9) |
| hydroxytetracosanoic | cerebronic | 2h-24:0 |
| hydroxytetracosenoic | hydroxynervonic | 2h15e-24:1 (n-9) |
| 3-hydroxybutyric | — | 3h-4:0 |
| hydroxyoctadecadienediynoic | isanolic | 8h9y11y17e-18:1 (n-2) |
| hydroxyoctadecenoic | strophanthus | 9h12c-18:1 (n-7) |
| hydroxyoctadecadienoic | β-dimorphecolic | 9h10t12t-18:2 (n-7) |
| 10-hydroxydecanoic | — | 10h-10:0 |
| hydroxydecenoic | royal jelly acid | 2t10h-10:1 (n-8) |
| hydroxyoctadecenoic | Ricinoleic | 9c12h-18:1 (n-9) |
| hydroxyoctadecadienoic | Densipolic | 9c12h15c-18:2 (n-4) |
| hydroxyoctadecadienoic | Coriolic | 9c11t13h-18:2 (n-8) |
| hydroxyeicosenoic | Lesquerolic | 11e14h-20:1 (n-10) |
| hydroxyeicosadienoic | Auricolic | 11e14h17e-20:2 (n-4) |
| hydroxyhexadecanoic | juniperic | 16h-16:0 |
| hydroxyoctadecatrienoic | kamlolenic | 9c1t13t18h-18:3 (n-5) |
| Polyhydroxy Fatty Acids | | |
| dihydroxytetracosenoic | axillarenic | 9e11h13h-24:1 (n-16) |
| dihydroxydocosanoic | byrsonic | 3h7h-22:0 |
| hydroxydocosanoic | phellonic | 22h-22:0 |
| trihydroxyoctadecanoic | phloionolic | 9h10h18h-8:0 |
| trihydroxyhexadecanoic | aleuritic | 9h10h16h-16:0 |
| trihydroxyicosahexaenoic | resolvin D1 | 4c7h8h9t11t13c15t17h19c-20:5 (n-4) |
| trihydroxyicosapentaenoic | resolvin E1 | 5h6t8t10t12h14c16t-20:5 (n-4) |
| Carboxy-Substituted Fatty Acids | | |
| ethanedioic | oxalic | 1,2dioic-2:0 |
| propanedioic | malonic | 1,3dioic-3:0 |
| butanedioic | succinic | 1,4dioic-4:0 |
| pentanedioic | glutaric | 1,5dioic-5:0 |
| hexanedioic | adipic | 1,6dioic-6:0 |
| heptanedioic | pimelic | 1,7dioic-7:0 |
| octanedioic | suberic | 1,8dioic-8:0 |
| nonanedioic | azelaic | 1,9dioic-9:0 |
| decanedioic | sebacic | 1,10dioic-10:0 |
| tridecanedioic | brassylic | 1,13dioic-13:0 |
| ethanedioic | oxalic | 1,2dioic-2:0 |
| propanedioic | malonic | 1,3dioic-3:0 |
| hexadecanedioic | thapsic | 1,16dioic-16:0 |
| methylidenebutanedioic | itaconic | 2Md1,4dioic-4:0 |
| methylbutenedioic | mesaconic | 2m2t1,4dioic-4:1 (n-2) |
| dodecenedioic | traumatic | 1,12dioic2t-12:1 (n-10) |
| dimethyltriacontanedioic | diabolic | 1,30dioic15m16m-30:0 |
| tetramethyl-hexadecaheptaenedioic | crocetin | 1,16dioic2m2t4t6m6t8t10t11m12t14 t15m-16:7 (n-2) |
| methyltetradecyl-butenedioic | chaetomellic acid A | 2m2c3a1,4dioic; a = —C$_{14}$H$_{29}$-4:1 (n-2) |
| methylidene-tetradecylbutanedioic | ceriporic acid A | 2Md3a1,4dioic; a = —C$_{14}$H$_{29}$-4:0 |
| Sulfate-Substituted Fatty Acids | | |
| disulfooxyhexadecanoic | caeliferin A16:0 | 2Sul16Sul-16:0 |
| disulfooxyhexadecenoic | caeliferin A16:1 | 2Sul6t16Sul-16:1 (n-10) |
| Methoxy-Substituted Fatty Acids | | |
| 2-methoxy-5-hexadecenoic | — | 2OMe5e-6:1 (n-1) |
| 2-methoxy hexadecanoic | — | 2OMe-16:0 |
| 7-methoxy-4-tetradecenoic | — | 4e7OMe-14:1 (n-10) |
| 9-methoxypentadecanoic | — | 9OMe-9:0 |

TABLE V-continued

Substituted fatty acids

| Systematic Name | Trivial Name | Shorthand Designation |
|---|---|---|
| 11-methoxyheptadecanoic | — | 11OMe-17:0 |
| 3-methoxydocosanoic | — | 3OMe-22:0 |
| Acetoxy-Substituted Fatty Acids | | |
| diacetoxydocosanoic | byrsonic | 3OAc7OAc-22:0 |
| 2-acetoxydocosanoic | — | 2OAc-22:0 |
| 2-acetoxytetracosanoic | — | 2OAc-24:0 |
| 2-acetoxyhexacosanoic | — | 2OAc-26:0 |
| Aldehyde-Substituted Fatty Acids | | |
| 9-oxononanoic | — | 9o-9:0 |
| oxodecanoic | traumatin | 12o-12:0 |
| oxododecenoic | traumatin | 9e12o-12:1 (n-3) |
| hydroxyoxodecenoic | hydroxytraumatin | 9h10e12o-12:1 (n-2) |
| 10-oxo-8-decenoic | — | 8t10o-10:1 (n-2) |
| 13-oxo-9,11-tridecadienoic | — | 9c11t13o-13:2 (n-2) |
| Halogenated Fatty Acids | | |
| Fluoro-Substituted Fatty Acids | | |
| fluorooctadecenoic | ω-fluorooleic | 9e18F-18:1 (n-9) |
| fluorodecanoic | ω-fluorocapric | 10F-10:0 |
| fluorotetradecanoic | ω-fluoromyristic | 14F-14:0 |
| fluorohexadecanoic | ω-fluoropalmitic | 16F-16:0 |
| fluorooctadecadienoic | ω-fluorolinoeic | 9c12c18F-18:2 (n-6) |
| Chloro-Substituted Fatty Acids | | |
| chlorohydroxyhexadecanoic | 9-chloro-10-hydroxypalmitic | 9Cl10h-16:0 |
| chlorohydroxyhexadecanoic | 10-chloro-9-hydroxypalmitic | 10Cl9h-16:0 |
| chlorohydroxyoctadecanoic | 9-chloro-10-hydroxystearic | 9Cl10h-18:0 |
| chlorohydroxyoctadecanoic | 11-chloro-12-hydroxystearic | 11Cl12h-18:0 |
| dichlorooctadecanoic | 9,10-dichlorostearic | 9Cl10Cl-18:0 |
| Bromo-Substituted Fatty Acids | | |
| 3-bromo-2-nonaenoic | — | 2e3Br-9:1 (n-7) |
| 9,10-dibromooctadecanoic | — | 9Br10Br-18:0 |
| 9,10,12,13-tetrabromooctadecanoic | — | 9Br10Br12Br13Br-18:0 |
| Nitro-Substituted Fatty Acids | | |
| 10-nitro-9,12-octadecadienoic | 10-nitrolinoleic | 9c10Nitro12c-18:2 (n-6) |
| 12-nitro-9,12-octadecadienoic | 12-nitrolinoleic | 9c12c12Nitro-18:2 (n-6) |
| 9-nitro-9-octadecenoic | 9-nitrooleic | 9c9Nitro-18:1 (n-9) |
| Keto-Substituted Fatty Acids | | |
| 9-oxo-2-decenoic | 9-ODA | 2t9k-10:1 (n-8) |
| 9-oxo-13-octadecenoic | — | 9k13e-18:1 (n-5) |
| oxooctadecatrienoic | licanic | 4k9c11t13t-18:3 (n-5) |
| 15-oxo-18-tetracosenoic | — | 15k18e-28:1 (n-6) |
| 17-oxo-20-hexacosenoic | — | 17k20e-26:1 (n-6) |
| 19-oxo-22-octacosenoic | — | 19k22e-28:1 (n-6) |
| 9-hydroxy-10-oxo-12,15-octadecadienoic | — | 9h10k12t15t-18:2 (n-3) |

TABLE VI

Heteroatom containing fatty acids

| Systematic name | Trivial name | Formula |
|---|---|---|
| Carbon Chain with Divinyl Ether Function | | |
| 9-(1,3-nonadienoxy)-8-nonenoic | colneleic | $CH_3(CH_2)_4CH=CHCH=CH-O-CH=CH(CH_2)_6CO_2H$ |
| 9-(1,3,6-nonatrienoxy)-8-nonenoic | colnelenic | $CH_3CH_2CH=CHCH_2CH=CHCH=CH-O-CH=CH(CH_2)_6CO_2H$ |
| 12-(1-hexenoxy)-9,11-dodecadienoic | etheroleic | $CH_3(CH_2)_3CH=CH-O-CH=CHCH=CH(CH_2)_7CO_2H$ |

TABLE VI-continued

Heteroatom containing fatty acids

| Systematic name | Trivial name | Formula |
| --- | --- | --- |
| 12-(1,3-hexadienoxy)-9,11-dodecadienoic | etherolenic | $CH_3CH_2CH=CHCH=CH-O-CH=CHCH=CH(CH_2)_7CO_2H$ |

Sulfur-Containing Carbon Chain

| Systematic name | Trivial name | Formula |
| --- | --- | --- |
| 2-dodecylsulfanylacetic | dodecylthioacetic | $CH_3(CH_2)_{11}-S-CH_2CO_2H$ |
| 2-tetradecylsulfanylacetic | tetradecylthioacetic (TTA) | $CH_3(CH_2)_{13}-S-CH_2CO_2H$ |
| 3-tetradecylsulfanylprop-2-enoic | tetradecylthioacrylic (TTAcr) | $CH_3(CH_2)_{13}-S-CH=CHCO_2H$ |
| 3-tetradecylsulfanylpropanoic | tetradecylthiopropionic (TTP) | $CH_3(CH_2)_{13}-S-(CH_2)_2CO_2H$ |

TABLE VII

Ring containing fatty acids

| Systematic Name | Trivial Name | Shorthand Designation |
| --- | --- | --- |
| *Fatty Acids with 3-Membered Rings* | | |
| *Cyclopropane Fatty Acids* | | |
| 10-(2-hexylcyclopropyl)decanoic | lactobacillic | 11-12m:18:0 |
| 8-(2-octylcyclopropyl)octanoic | — | 9-10m:18:0 |
| 8-(2-hexylcyclopropyl)octanoic | — | 9-10m-16:0 |
| 3-(2-[6-bromo-3,5-nondienylcyclopropyl)propanoic | majusculoic | 4-5m8t10t11Br-14:2 (n-4) |
| 9-(2-hexadecylcyclo-propylidene)non-5-enoic | amphimic acid A | 5c9t10-11m-27:2 (n-18) |
| *Cyclopropene Fatty Acids* | | |
| 8-(2-octyl-1-cyclopropenyl)octanoic | sterculic | 9e9-10m-18:1 (n-9) |
| 7-(2-octyl-1-cyclopropenyl)heptanoic | malvalic | 8e8-9m-17:1 (n-9) |
| *Epoxy Fatty Acids* | | |
| 9,10-epoxyoctadecanoic | 9,10-epoxystearic | 9-10epoxy-18:0 |
| 9,10-epoxy12-octadecenoic | coronaric | 9-10epoxy12e-18:1 (n-6) |
| 12,13-epoxy-9-octadecenoic | vernolic | 9e12-13epoxy-18:1 (n-9) |
| 14,15-epoxy-11-eicosenoic | alchornic | 11e14-15epoxy-20:1 (n-9) |
| 8-hydroxy-11,12-epoxy-5,9,14-eicosatrienoic | hepoxilin A3 | 5t8h9t11-12epoxy14t-20:3 (n-6) |
| *Fatty Acids with 5-Membered Rings* | | |
| 11-(2-cyclopenten-1-yl)undecanoic | hydnocarpic | |
| 13-(2-cyclopenten-1-yl)tridecanoic | chaulmoogric | |
| 13-(2-cyclopentenyl)-6-tridecenoic | gorlic | |
| 9-(2-(but-1-enyl)cyclopentyl)nonanoic | — | |

TABLE VII-continued

Ring containing fatty acids

| Systematic Name | Trivial Name | Shorthand Designation |
|---|---|---|
| 3-methyl-6-(3-(6-methylheptan-2-yl)-cyclopentypexanoic | | structure with cyclopentane, isoheptyl chain and $CO_2H$ terminus |
| 2-(3'-(6-methylheptan-2-yl)-bi(cyclopentan)-3-yl)acetic | | structure with bi-cyclopentane, isoheptyl chain and $CO_2H$ terminus |

Fatty Acids with 6-Membered Rings

| Systematic Name | Trivial Name | Shorthand Designation |
|---|---|---|
| 11-cyclohexylundecanoic | — | cyclohexyl–$(CH_2)_{10}CO_2H$ |
| 13-cyclohexyltridecanoic | — | cyclohexyl–$(CH_2)_{12}CO_2H$ |
| 9-(6-(prop-1-enyl)cyclohex-3-enyl)-nonanoic | — | $CH_3CH{=}CH$–cyclohexenyl–$(CH_2)_8CO_2H$ |
| 8-(6-(3-pentenyl)-3-cyclohexenyl)-5,7-octadienoic | — | pentenyl–cyclohexenyl–octadienoic $CO_2H$ |

Furan Containing Fatty Acids

| Systematic Name | Trivial Name | Shorthand Designation |
|---|---|---|
| 7-(3,4-dimethyl-5-pentylfuran-2-yl)heptanoic | — | $CH_3(CH_2)_4$–(3,4-dimethylfuran)–$(CH_2)_6CO_2H$ |
| 9-(4-methyl-5-pentylfuran-2-yl)nonanoic | — | $CH_3(CH_2)_4$–(4-methylfuran)–$(CH_2)_8CO_2H$ |
| 11-(3,4-dimethyl-5-propylfuran-2-yl)undecanoic | — | $CH_3(CH_2)_2$–(3,4-dimethylfuran)–$(CH_2)_{10}CO_2H$ |
| 11-(4-methyl-5-pentylfuran-2-yl)undecanoic | — | $CH_3(CH_2)_4$–(4-methylfuran)–$(CH_2)_{10}CO_2H$ |

TABLE VII-continued

Ring containing fatty acids

| Systematic Name | Trivial Name | Shorthand Designation |
|---|---|---|
| 2-(2-carboxyethyl)-4-methyl-5-propylfuran-3-carboxylic | — | $CH_3(CH_2)_2$—furan—$(CH_2)_2CO_2H$, $CO_2H$ |
| 3,3'-(3,4-dimethylfuran-2,5-diyl)dipropanoic | — | $HO_2C(CH_2)_2$—furan—$(CH_2)_2CO_2H$ |

Ladderane Containing Fatty Acids

| Systematic Name | Trivial Name | Shorthand Designation |
|---|---|---|
| 4-[5]-ladderane-butanoic | — | [5]-ladderane-$(CH_2)_3CO_2H$ |
| 6-[5]-ladderane-hexanoic | — | [5]-ladderane-$(CH_2)_5CO_2H$ |
| 8-[5]-ladderane-octanoic | — | [5]-ladderane-$(CH_2)_7CO_2H$ |
| 6-[3]-ladderane-hexanoic | — | [3]-ladderane-cyclohexane-$(CH_2)_5CO_2H$ |

In one embodiment, the fatty acid conjugated to quetiapine, its active metabolite or derivative used in the compositions, systems and methods described herein, is any one of the fatty acids in Tables I-VII provided herein, or a combination thereof. Accordingly and in one embodiment, provided herein is a composition for treating a psychiatric disorder in a subject, comprising a conjugate of 2-(2-(4-(dibenzo[b,f][1,4]thiazepin-11-yl)piperazin-1-yl)ethoxy) ethanol (quetiapine) and at least one saturated fatty acid. In another embodiment, quetiapine is conjugated to at least one monounsaturated fatty acid, or a polyunsaturated fatty acid in another embodiment, or an acetylenic fatty acid, a substituted fatty acid, a heteroatom containing fatty acid, a ring containing fatty acid; a salt thereof, a derivative thereof or their combination in other, discrete embodiments of the conjugates of quetiapine provided herein.

In another embodiment, the fatty acid conjugated to quetiapine or its active metabolite, used in the compositions and methods described herein, is a saturated fatty acid such as palmitic acid in one embodiment, a monounsaturated fatty acid such as palmitoleic acid in another embodiment, a polyunsaturated fatty acid such as DHA in yet another discrete embodiment of the fatty acid conjugated to quetiapine according to the invention.

In one embodiment, the active metabolite of quetiapine is N-desalkyl-quetiapine (norQTP).

(norQTP)

norQTP is a major active human plasma metabolite of quetiapine, which has shown in-vitro antagonistic activity on multiple brain neurotransmitter receptors and in particular on serotonergic (5-$HT_{2A}$), adrenergic ($\alpha_1$-adrenoreceptor) and the noradrenergic transporter, thus having in another embodiment, a positive influence on mood. Likewise, N-desalkyl-quetiapine, has a high affinity for the histamine $H_1$ receptor and moderate affinities for the norepinephrine reuptake transporter (NET), the serotonin 5-$HT_{1A}$, 5-$HT_{1E}$, 5-$HT_{2A}$, 5-$HT_{2B}$, 5-$HT_7$ receptors, the $\alpha_{1B}$-adrenergic receptor, and the $M_1$, $M_3$, and $M_5$ muscarinic receptors. In one embodiment, N-desalkyl-quetiapine has about 100-fold higher avidity for inhibiting human NET than quetiapine itself. Additionally, N-desalkyl-quetiapine is 10-fold more potent and more efficacious than quetiapine at the 5-$HT_{1A}$ receptor. N-Desalkyl-quetiapine is an antagonist at 5-$HT_{2A}$, 5-HT$_{2B}$, 5-HT$_{2C}$, α$_{1A}$, α$_{1D}$, α$_{2A}$, α$_{2C}$, H$_1$, M$_1$, M$_3$, and M$_5$ receptors, with a moderate affinity for the norepinephrine reuptake inhibitor transporter (NET) and partial 5-HT1$_A$ agonism, indicating a significant antidepressant effects. In one embodiment, the compositions provided herein, which in another embodiment are used in the methods provided herein comprise the N-desalkyl-quetiapine, conjugated to a saturated fatty acid such as valproate, or a monounsaturated fatty acid, a polyunsaturated fatty acid, an acetylenic fatty acid, a substituted fatty acid, a heteroatom containing fatty acid, a ring containing fatty acid or a combination thereof, each a discrete embodiment of the fatty acid conjugates without the presence of quetiapine.

In one embodiment, the active metabolite of quetiapine is 7-hydroxy-quetiapine (7-OH-QTP).

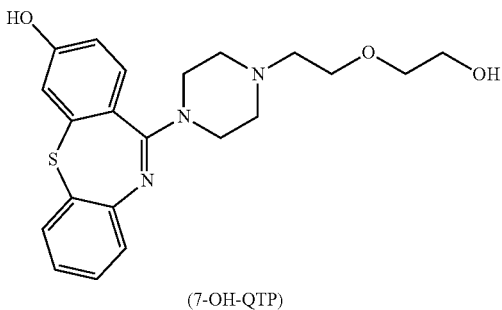 [SMILES: OCCOCCN1CCN(C2=Nc3ccccc3Sc3cc(O)ccc32)CC1]

(7-OH-QTP)

7-OH-QTP is another active human plasma metabolite of quetiapine having intrinsic receptor activity. 7-hydroxy-quetiapine has been shown to occupy dopamine D$_2$ and serotonin 5-HT$_2$ receptors. In one embodiment, the compositions provided herein, which in another embodiment is used in the methods provided herein comprise 7-hydroxy-quetiapine, conjugated to a saturated fatty acid, or a monounsaturated fatty acid, a polyunsaturated fatty acid, an acetylenic fatty acid, a substituted fatty acid, a heteroatom containing fatty acid, a ring containing fatty acid or a combination thereof, each a discrete embodiment of the fatty acid conjugated to 7-OH-QTP, without the presence of quetiapine.

In another embodiment, the term "derivative" refers to having a substituent bonded to quetiapine or its active metabolite such as halogenated derivatives ether derivatives, acid derivatives, amide derivatives, ester derivatives and the like. Methods of preparing derivatives such as ether derivatives in one embodiment comprise coupling of the corresponding alcohols. In another embodiment, the term "derivative" refers to a chemical compound related structurally to quetiapine or its active metabolites and is therapeutically derivable from it. In one embodiment, the term "active derivative" refers to a derivative as defined herein, which is accountable for a desired biological effect. Accordingly, an active derivative of quetiapine will have in one embodiment an antipsychotic activity, or an antidepressant activity and the like in other embodiments of desired biological effects.

In one embodiment, the active derivative of quetiapine is 2-chloro-N-desalkyl-quetiapine (2-Cl-norQTP).

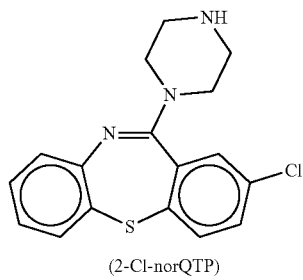

(2-Cl-norQTP)

2-Cl-norQTP a derivative of norQTP, which, due to its similar structure to the known antidepressant amoxapine, is thought to possess similar psychiatric activity as a norepinephrine reuptake inhibitor and/or as a partial 5-HT agonist. In one embodiment, the compositions provided herein, which in another embodiment is used in the methods provided herein comprise 2-chloro-N-desalkyl-quetiapine, conjugated to a saturated fatty acid, a monounsaturated fatty acid, a polyunsaturated fatty acid, an acetylenic fatty acid, a substituted fatty acid, a heteroatom containing fatty acid, a ring containing fatty acid and/or its pharmaceutically acceptable salt, without the presence of quetiapine; and/or active metabolites thereof.

In one embodiment, using 2-Cl-norQTP conjugated to a saturated fatty acid, or a monounsaturated fatty acid, a polyunsaturated fatty acid, an acetylenic fatty acid, a substituted fatty acid, a heteroatom containing fatty acid, a ring containing fatty acid or a combination thereof, each a discrete embodiment of the fatty acid conjugated to 2-Cl-norQTP; does not lower the seizure threshold to the extent that fits may be precipitated in chronic administration, especially in children.

In one embodiment, the active derivative of quetiapine is 7-hydroxy-N-desalkylquetiapine (7-OH-norQTP).

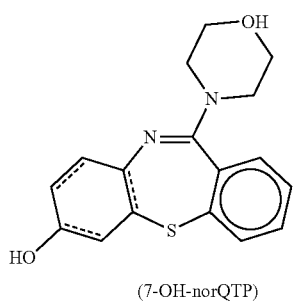

(7-OH-norQTP)

7-OH-norQTP a derivative of norQTP, which, due to its similar structure to the known active quetiapine metabolite 7-hydroxy-quetiapine, is thought to possess similar activities. In one embodiment, the compositions provided herein, which in another embodiment is used in the methods and transdermal systems provided herein comprise 7-hydroxy-N-desalkyl-quetiapine, conjugated to a saturated fatty acid, or a monounsaturated fatty acid, a polyunsaturated fatty acid, an acetylenic fatty acid, a substituted fatty acid, a heteroatom containing fatty acid, a ring containing fatty acid or a combination thereof and/or its pharmaceutically acceptable salt, each a discrete embodiment of the 7-OH-norQTP conjugates provided herein, without the presence of quetiapine; and/or active metabolites thereof.

In one embodiment, the fatty acid is acetic acid and the conjugate is 2-(2-(4-(dibenzo[b,f][1,4]thiazepin-11-yl)piperazin-1-yl)ethoxy)ethyl acetate, 2-(2-(4-(7-hydroxydibenzo[b,f][1,4]thiazepin-11-yl)piperazin-1-yl)ethoxy)ethyl acetate, 1-(4-(dibenzo[b,f][1,4]thiazepin-11-yl)piperazin-1-yl)ethanone, 1-(4-(7-hydroxydibenzo[b,f][1,4]thiazepin-11-yl)piperazin-1-yl)ethanone; their derivative, pharmaceutically acceptable salt or their combination.

In one embodiment, the fatty acid is butyric acid and the conjugate is 2-(2-(4-(dibenzo[b,f][1,4]thiazepin-11-yl)piperazin-1-yl)ethoxy)ethyl butyrate, 2-(2-(4-(7-hydroxydibenzo[b,f][1,4]thiazepin-11-yl)piperazin-1-yl)ethoxy)ethyl butyrate, 1-(4-(dibenzo[b,f][1,4]thiazepin-11-yl)piperazin-1-yl)butan-1-one, 1-(4-(7-hydroxydibenzo[b,f][1,4]thiazepin-11-yl)piperazin-1-yl)butan-1-one; their derivative, pharmaceutically acceptable salt or their combination.

In another embodiment, the fatty acid is valeric acid, and the conjugate is 2-(2-(4-(dibenzo[b,f][1,4]thiazepin-11-yl)piperazin-1-yl)ethoxy)ethyl valerate, 2-(2-(4-(7-hydroxydibenzo[b,f][1,4]thiazepin-11-yl)piperazin-1-yl)ethoxy)ethyl valerate, 1-(4-(dibenzo[b,f][1,4]thiazepin-11-yl)piperazin-1-yl)pentan-1-one, 1-(4-(7-hydroxydibenzo[b,f][1,4]thiazepin-11-yl)piperazin-1-yl)pentan-1-one; their derivative, pharmaceutically acceptable salt or their combination.

In one embodiment, the fatty acid is caprylic acid and the conjugate is 2-(2-(4-(dibenzo[b,f][1,4]thiazepin-11-yl)piperazin-1-yl)ethoxy)ethyl caprylate, 2-(2-(4-(7-hydroxydibenzo[b,f][1,4]thiazepin-11-yl)piperazin-1-yl)ethoxy)ethyl caprylate, 1-(4-(dibenzo[b,f][1,4]thiazepin-11-yl)piperazin-1-yl)octan-1-one, 1-(4-(7-hydroxydibenzo[b,f][1,4]thiazepin-11-yl)piperazin-1-yl)octan-1-one; their derivative, pharmaceutically acceptable salt or their combination.

In one embodiment, the saturated fatty acid conjugated to quetiapine, its active metabolite and/or active derivative, their pharmaceutically acceptable salt and/or their combination is any one of the fatty acids provided in Table I herein. In another aspect, the monounsaturated fatty acid conjugated to quetiapine, its active metabolite and/or active derivative, their pharmaceutically acceptable salt and/or their combination is selected from the group consisting of any one of the fatty acids set forth in Table II. In another aspect, the polyunsaturated fatty acid conjugated to quetiapine, its active metabolite and/or active derivative, their pharmaceutically acceptable salt and/or their combination is selected from the group consisting of any one of the fatty acids set forth in Table III. In one embodiment, the acetylenic fatty acid conjugated to quetiapine, its active metabolite and/or active derivative, their pharmaceutically acceptable salt and/or their combination is selected from the group consisting of any one of the fatty acids set forth in Table IV.

In one embodiment, the substituted fatty acid conjugated to quetiapine, its active metabolite and/or active derivative, their pharmaceutically acceptable salt and/or their combination is an alkyl-substituted fatty acid. In another embodiment, the substituted fatty acid conjugated to quetiapine, its active metabolite and/or active derivative, their pharmaceutically acceptable salt and/or their combination is a hydroxy-substituted fatty acid, carboxy-substituted fatty acid, halogenated fatty acid, sulfate-substituted fatty acid, methoxy-substituted fatty acid, acetoxy-substituted fatty acid, aldehyde-substituted fatty acid, nitro-substituted fatty acid, or keto-substituted fatty acid, each a discrete embodiment of the substituted fatty acid conjugated to quetiapine, its active metabolite and/or active derivative, their pharmaceutically acceptable salt and/or their combination. In another aspect, the substituted fatty acid conjugated to quetiapine, its active metabolite and/or active derivative, their pharmaceutically acceptable salt and/or their combination is selected from the group consisting of any one of the fatty acid compounds set forth in Table V.

In one embodiment, the heteroatom containing fatty acid conjugated to quetiapine, its active metabolite and/or active derivative, their pharmaceutically acceptable salt and/or their combination has a carbon chain containing a divinyl ether function. In another embodiment, the heteroatom containing fatty acid conjugated to quetiapine, its active metabolite and/or active derivative, their pharmaceutically acceptable salt and/or their combination has a carbon chain containing a sulfur function. In another aspect, the heteroatom containing fatty acid conjugated to quetiapine, its active metabolite and/or active derivative, their pharmaceutically acceptable salt and/or their combination, is selected from the group consisting of any one of the fatty acid compounds set forth in Table VI.

In one embodiment, the ring containing fatty acid conjugated to quetiapine, its active metabolite and/or active derivative, their pharmaceutically acceptable salt and/or their combination is a fatty acid containing at least one three-membered ring, a fatty acid containing at least one five-membered ring, a fatty acid containing at least one six-membered ring, a fatty acid containing ladderanes, a fatty acid containing at least one furan ring or a combination thereof, each a discrete embodiment of the ring containing fatty acid conjugated to quetiapine, its active metabolite and/or active derivative, their pharmaceutically acceptable salt and/or their combination. In another aspect, the ring containing fatty acid conjugated to quetiapine, its active metabolite and/or active derivative, their pharmaceutically acceptable salt and/or their combination, is selected from the group consisting of any one of the fatty acid compounds set forth in Table VII.

Fatty acid ester prodrugs of quetiapine as described above can be administered orally and the active drug is released after hydrolysis in the body. In one embodiment, these prodrugs are easily recognized by physiological systems because the attached fatty acid moieties are either naturally occurring or mimic naturally occurring compounds. As a result, the prodrugs provided herein are hydrolyzed chemically, enzymatically or by a combination of chemical and enzymatic processes; and release quetiapine. In another embodiment the compositions comprising the prodrugs described herein, are either pharmacologically inactive, have pharmacological activity that is limited or different from the parent drug, and consequently, in certain embodiments, may follow a metabolic pathway that differs from quetiapine. In another aspects, both quetiapine and the fatty acid are therapeutically active in the subject In another embodiment, the term "prodrug" refers to a precursor or derivative form of a pharmaceutically active substance that imparts higher bioavailability to quetiapine compared to the parent drug and is capable of being enzymatically or hydrolytically activated or converted into the more active parent form. In one embodiment, the compositions comprising the prodrugs described herein would release quetiapine in a similar fashion to free or unconjugated quetiapine. In another embodiment, the compositions comprising the prodrugs described herein would release quetiapine in a controlled or sustained manner without the need of an extended release formulation. In another aspect, sustained or controlled release is obtained by conjugating quetiapine as described herein to a functionalized fatty acid capable of being cross-linked, whereby the degree of cross-linking affect the rate of release of quetiapine, its active metabolite and/or active derivative, by affecting the diffusion rate of the enzyme or chemical agent affecting the hydrolysis of the conjugate in one embodiment.

In a further embodiment, the compositions comprising the prodrugs described herein would have increased absorption over unmodified quetiapine. In another embodiment, the increased absorption over unmodified quetiapine, or improved water solubility over free quetiapine, provide for a better bioavailability of quetiapine referring to a higher AUC or higher circulating plasma concentrations.

In yet another embodiment, the compositions comprising the prodrugs described herein would have increased bioavailability over unconjugated quetiapine. This may allow for administration of a lower dose with equal or improved therapeutic effect, but with fewer and/or less severe side-effects when compared to unmodified quetiapine, thereby improving the safety profile of the drug. Common adverse side-effects associated with quetiapine include sedation, constipation, dizziness, dry mouth, lightheadedness, nasal congestion, sore throat, stomach pain or upset, tiredness, vomiting, weakness, weight gain, hyperlipidemia, hypotension, hyperglycemia and more. In one embodiment, the use of the compositions described herein results in elimination, amelioration, reduction or improvement in common side-effects associated with chronic or acute administration of quetiapine.

In another embodiment, the compositions comprising the prodrugs described herein would reduce weight gain when compared to unconjugated quetiapine. Accordingly and in one embodiment, the invention provides a method of reducing weight gain resulting from chronic or acute administration of quetiapine in a subject, comprising the step of orally, transdermally or rectally administering to the subject a composition comprising a therapeutically effective amount of about 1-2000 mg/dose based on equimolar weight of unconjugated quetiapine; of quetiapine or its active metabolite and/or active derivative thereof such as 7-hydroxy-N-desalkyl-quetiapine, or 7-hydroxy-quetiapine, conjugated to a saturated fatty acid, a monounsaturated fatty acid, a polyunsaturated fatty acid, an acetylenic fatty acid, a substituted fatty acid, a heteroatom containing fatty acid, a ring containing fatty acid, a pharmaceutically acceptable salt thereof, or derivative thereof, or their combination, thereby modulating leptin and/or ghrelin levels, or in another embodiment, altering the metabolism of quetiapine, its metabolite(s) and/or derivative(s), resulting in reduced binding to histamine receptor(s) in the subject and thereby eliminating, reducing, delaying, decreasing and/or inhibiting weight gain in the subject.

In one embodiment, chronic oral administration of quetiapine, a known orexigenic, for a period of 6 weeks causes about 37% increase in leptin release. In another aspect, conjugating an active metabolite and/or derivative of quetiapine to a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof, will modulate the release of leptin and/or ghrelin, resulting in certain embodiments with lower weight gain or lower increase in body/mass index (BMI). Since ghrelin regulates the release of leptin in certain embodiments, and is released in response to fasting and cachexia, ingestion of at least one fatty acid conjugate of quetiapine as set forth in Tables I-VII, will decrease its release, resulting in lower weight gain.

In another embodiment, the compositions comprising the conjugates described herein would generate a $C_{max}$ value of released quetiapine that is higher than the $C_{max}$ value produced by unconjugated quetiapine when administered at equimolar doses (See e.g., FIG. 1). In a further embodiment, the compositions comprising the prodrugs described herein would generate an AUC value of released quetiapine that is higher than the AUC value produced by unconjugated quetiapine when administered at equimolar doses. In yet another aspect, the compositions comprising the prodrugs described herein would generate both a $C_{max}$ and an AUC value of released quetiapine that is higher than the $C_{max}$ and AUC values produced by unconjugated quetiapine when administered at equimolar doses.

In another embodiment the compositions comprising the conjugates described herein would generate a $T_{max}$ value of released quetiapine that is longer than the $T_{max}$ value produced by unconjugated quetiapine when administered at equimolar doses. In another embodiment the compositions comprising the prodrugs described herein would generate a $T_{max}$ value of released quetiapine that is similar to the $T_{max}$ value produced by unconjugated quetiapine, when administered at equimolar doses.

In another embodiment, the compositions comprising the prodrugs described herein would have reduced interindividual variability either due to increased bioavailability in one aspect, or due to a modified metabolic pathway in another aspect, or due to a combination of both in yet another aspect.

In another embodiment, the compositions comprising the prodrugs described herein would alter the metabolic pathway of the released quetiapine when compared to unmodified quetiapine. This new metabolism may decrease interindividual variability and/or reduce side-effects associated with unconjugated quetiapine or any of its metabolites, pharmaceutically acceptable salts, derivatives thereof or their combination.

In yet another embodiment, the compositions comprising the prodrugs described herein would decrease the number and/or amount of metabolites—active, inactive, toxic or non-toxic—produced by unmodified quetiapine. This may decrease interindividual variability and/or reduce side-effects associated with the administration of unconjugated quetiapine.

In a further embodiment, the compositions comprising the prodrugs described herein would increase the amount of active metabolites when compared to unmodified quetiapine. This may improve the therapeutic efficacy of the parent drug.

Although quetiapine is not a controlled substance, there have been increasing reports of its misuse via oral, intranasal, and intravenous routes to exploit its potent sedative and anxiolytic properties. Some of its street names include "quell", "baby heroin" and "Susie-Q". In some embodiments, the compositions comprising the prodrugs described herein may not be hydrolyzed efficiently when administered by non-oral routes. As a result, these prodrugs may generate plasma concentrations of released quetiapine that are lower when compared to free quetiapine administered intravenously ("injected") or intranasally ("snorted"). Accordingly, by altering the metabolic pathway the conjugated compounds provided herein may decrease the potential for abuse of quetiapine.

In one embodiment provided herein, quetiapine or its active metabolite, is conjugated to at least one fatty acid as represented by any one of the structures of formulas I-IV:

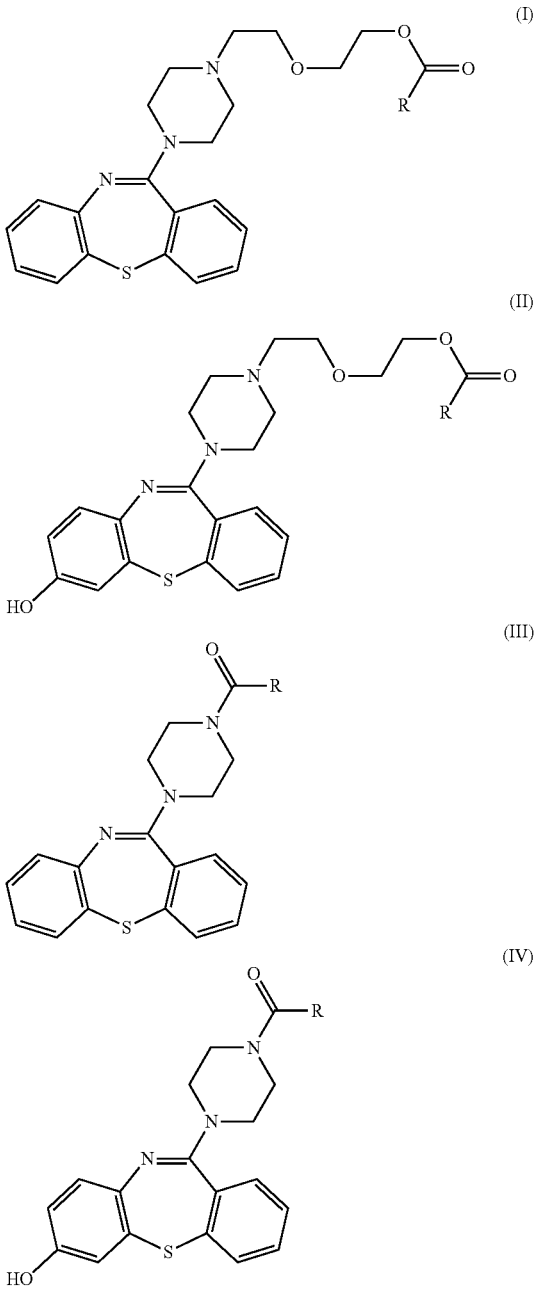

a pharmaceutically acceptable salt thereof, a derivative thereof or a combination thereof, wherein "R" is a fatty acid side-chain selected from the group consisting at least one of the fatty acids set forth in Tables I-VII.

In one embodiment, the salt of the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof, such as any one of the structures represented by formulas I-IV hereinabove, and the fatty acid represented by any of the compounds in Tables I-VII, is an acetate salt. In another aspect, the salt of the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof is L-aspartate, or besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate or a mixture thereof, in other discrete embodiments of the salts of the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof comprising the compositions and used in the methods and systems provided herein.

Formulation Examples

In one embodiment, the composition comprising the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof is formulated for oral administration. In another aspect, the composition comprising the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof is formulated for sublingual, or transdermal, intrathecal or a suppository administration in other discrete formulation embodiments of the compositions provided herein and are used in the systems and methods described herein.

In one embodiment, the term "intrathecal administration" refers to the delivery of an active compound formulation directly into the cerebrospinal fluid of a subject, by lateral cerebroventricular injection through a burr hole or cisternal or lumbar puncture or the like (described in Lazorthes et al., 1991, and Ommaya A. K., 1984, the contents of which are incorporated herein by reference in its entirety). The term "lumbar region" refers to the area between the third and fourth lumbar (lower back) vertebrae. The term "cisterna magna" refers to the area where the skull ends and the spinal cord begins at the back of the head. The term "cerebral ventricle" refers to the cavities in the brain that are continuous with the central canal of the spinal cord. Administration of quetiapine, its active metabolite(s) and/or derivative(s) conjugated to a saturated fatty acid such as valproic acid, a monounsaturated fatty acid, a polyunsaturated fatty acid such as DHA and/or EPA, an acetylenic fatty acid, a substituted fatty acid, a heteroatom containing fatty acid, a ring containing fatty acid or a combination thereof to any of the above mentioned sites can be achieved by direct injection of the active compound formulation or by the use of infusion pumps. Implantable or external pumps and catheter may be used.

The prodrugs provided in the compositions and methods herein are geared in one embodiment, towards oral dosage forms. These dosage forms include but are not limited to a tablet, capsule, caplet, pill, powder, troche, lozenge, slurry, liquid solution, suspension, emulsion, elixir or oral thin film (OTF), each a discrete aspect of the oral dosage form used in the compositions and methods provided herein. Preferred oral administration forms are capsule in one embodiment, or tablet, solutions and OTF in certain other embodiments. The film dosage forms provide an inexpensive, convenient and immediate method for delivery of the compositions described herein without the undesirable aspects associated with certain oral or nasal delivery methods, while providing versatility, safety and patient comfort. Any effective edible "thin film" or "strip" may be used in accordance with the present invention. Unless otherwise specified or required by the context, the edible films of the present invention may be manufactured in any effective manner.

In certain aspects, the film layer can be produced using a highly water-soluble polymer comprising a natural or synthetic water-soluble polymer. The polymer preferably has good film moldability, produces a soft flexible film, and is safe for human consumption. In another embodiment, one such polymer can be a water-soluble cellulose derivative like hydroxypropyl cellulose (HPC), methyl cellulose, hydroxypropyl alkylcellulose, carboxymethyl cellulose or the salt of carboxymethyl cellulose. Or, the polymer can comprise an acrylic acid copolymer or its sodium, potassium or ammonium salt. The acrylic acid copolymer or its salt can be combined with methacrylic acid, styrene or a vinyl type of ether as a comonomer, polyvinyl alcohol, polyvinylpyrrolidone, polyalkylene glycol, hydroxypropyl starch, alginic acid or its salt, polysaccharide or its derivatives such as tragacanth, gum gelatin, collagen, denatured gelatin, and collagen treated with succinic acid or anhydrous phthalic acid. In another embodiment the powder matrix may comprise as adhesives: poorly water-soluble cellulose derivatives including ethyl cellulose, cellulose acetate and butyl cellulose; shellac; higher fatty acids including stearic acid and palmitic acid. The following can also, without limitation, be used to produce the film layer: pullulan, maltodextrin, pectin, alginates, carrageenan, guar gum, other gelatins, etc. The thickness of the film layer can vary as desired, but typically is in the range of 0.01 mm to 3.00 mm, preferably 0.03 mm to 1.00 mm. In one embodiment, the saturated fatty acid, or monounsaturated fatty acid, polyunsaturated fatty acid, acetylenic fatty acid, substituted fatty acid, heteroatom containing fatty acid, ring containing fatty acid or their combination in other discrete embodiments that are used in the conjugate of quetiapine or an active metabolite and/or derivative thereof provided herein will be affected by the composition of the OTF.

Solid dosage forms can include the following types of excipients: antiadherents, binders, coatings, disintegrants, fillers, flavors and colors, glidants, lubricants, preservatives, sorbents and sweeteners.

For oral administration, the conjugates can be formulated readily by combining the active compounds with pharmaceutically acceptable carriers well known in the art. Such carriers enable the conjugates provided herein to be formulated as tablets, pills, dragées, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragée cores. Suitable excipients are, in certain embodiments, fillers such as sugars, including lactose, sucrose, manioc, or sorbitol; cellulose preparations such as, for example, maize starch, wheat starch, rice starch, potato starch, gelatin, gum tragacanth, methyl cellulose, hydroxypropyl methyl cellulose, sodium carboxymethyl cellulose and/or physiologically acceptable polymers such as polyvinylpyrrolidone (PVP). If desired, in certain embodiments disintegrating agents may be added, such as cross-linked polyvinylpyrrolidone, agar, or alginic acid or a salt thereof such as sodium alginate.

Dragée cores may be provided with suitable coatings. For this purpose, concentrated sugar solutions may be used which may optionally contain gum arabic, talc, polyvinylpyrrolidone, carbopol gel, polyethylene glycol, titanium dioxide, lacquer solutions and suitable organic solvents or solvent mixtures. Dyestuffs or pigments may be added to the tablets or dragée coatings for identification or to characterize different combinations of active compound doses.

For buccal administration, the compositions may take the form of tablets or lozenges formulated in conventional manner. Alternatively, the active ingredient may be in powder form for constitution with a suitable vehicle, e.g., sterile, pyrogen-free water (e.g., WFI USP), before use. The conjugates provided herein may also be formulated in rectal compositions such as suppositories or retention enemas, using, e.g., conventional suppository bases such as cocoa butter or other glycerides.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with fillers such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Quetiapine was originally launched as an immediate release product (Seroquel®) with the following dosage strengths per tablet: 25 mg, 50 mg, 100 mg, 200 mg and 300 mg. Recommended daily doses typically range from 150-800 mg depending on indication and individual patient titration. In another embodiment, quetiapine is available in an extended release formulation (Seroquel XR®) with dosage strengths of 50 mg, 150 mg, 200 mg, 300 mg and 400 mg per tablet. Typical daily doses range from 300-800 mg.

In one embodiment, the compositions provided herein are formulated for transdermal delivery, such as a patch in one embodiment. In another embodiment, the term "transdermal delivery" refers to the transport of the composition comprising the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid or a combination thereof across the epidermis, where the compound is absorbed in the blood capillaries. In another aspect, transdermal delivery refers to the administration of the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid or a combination thereof in a transdermal therapeutic system, comprising a drug reservoir matrix comprised essentially of a) a gelling agent that is selected from the group consisting of carbomer, carboxyethylene, polyacrylic acid, cellulose derivatives, ethylcellulose, hydroxypropyl methyl cellulose, ethyl hydrooxyethyl cellulose, carboxymethyl cellulose, hydroxypropyl cellulose, hydroxyethyl cellulose, natural gums, arabic, xanthan, guar gums, alginates, polyvinylpyrrolidone derivatives, polyoxyethylene polyoxypropylene copolymers, chitosan, polyvinyl alcohol, pectin, or veegum; and b) quetiapine, an active metabolite or derivative thereof and therapeutically acceptable salts thereof, and mixtures thereof; conjugated to at least one of a permeation enhancer.

In one aspect, a transdermal patch is a skin patch which includes the conjugate of quetiapine, its active metabolite and/or active derivative, their pharmaceutically acceptable salt and/or their combination and which may be applied to the skin of the subject. Many types of materials and designs for the transdermal drug delivery have been extensively described, see e.g., D. Hsien, "Multiple Lamination for Transdermal Patches," Controlled Released Systems Fabrication Technology, v. 1, pp. 167-188 (1988), incorporated herein by reference in its entirety.

In one embodiment, the compositions comprising the conjugates of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid or a combination thereof described herein are transferred by diffusion, in the presence of permeation enhancers in another embodiment. In other aspects, the conjugate of quetiapine or an active metabolite and/or derivative thereof and a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid or a combination thereof described herein may be transferred from the transdermal patch by iontophoresis or electroosmosis in other discrete aspects of the transfer mode encompassed by the systems described herein. Iontophoresis is based on the transport of charged ions by coulombic attraction/repulsion in an electric field. In one embodiment, iontophoresis induces an increased migration of ions or charged molecules such as salts of the conjugates described herein in an electrolyte medium in the presence of the flow of electric current. Many transdermal patches which utilize iontophoresis for transport of drugs have been described such as, for example, U.S. Pat. No. 5,527,797, incorporated herein by reference in its entirety.

To effectively permeate the skin in a transdermal delivery system, the drug sought to be delivered should pass through the stratum corneum (SC), a protective layer of skin that is significantly resistant to permeation of hydrophilic material. In one embodiment, passive drug diffusion is enhanced through modification of the nature of the drug molecule to facilitate permeation, such as the conjugation of the API to at least one fatty acid. In another aspect, the fatty acid conjugated to quetiapine and/or its active metabolite and/or its active derivative(s) used in the transdermal delivery systems described herein is a short-chain fatty acid such as valproic acid in one embodiment, a medium-chain fatty acid such as lauric acid in another embodiment, a long-chain fatty acid such as stearic acid in another embodiment, or a combination thereof in yet another embodiment. In another embodiment, the fatty acid conjugated to quetiapine and/or its active metabolite and/or its active derivative(s) used in the transdermal delivery systems described herein is a saturated fatty acid, a monounsaturated fatty acid, a polyunsaturated fatty acid, an acetylenic fatty acid, a substituted fatty acid, a heteroatom containing fatty acid, or a ring containing fatty acid, or a combination thereof.

The term "stratum corneum" is used herein in its broadest sense to refer to the outer layer of the skin, which is comprised of (approximately of 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the API across the skin.

Accordingly and in one embodiment, provided herein is a quetiapine transdermal therapeutic system, comprising a drug reservoir comprised essentially of a) a gelling agent that is selected from the group consisting of carbomer in one embodiment, or carboxyethylene, polyacrylic acid, cellulose derivatives, ethyl cellulose, hydroxypropyl methyl cellulose, ethyl hydroxyethyl cellulose, carboxymethyl cellulose, hydroxypropyl cellulose, hydroxyethyl cellulose, natural gums, arabic, xanthan, guar gums, alginates, polyvinylpyrrolidone derivatives, polyoxyethylene polyoxypropylene copolymers, chitosan, polyvinyl alcohol, pectin, or veegum, or their combination in other discrete embodiments; and b) quetiapine, an active metabolite or derivative thereof and therapeutically acceptable salts thereof, and mixtures thereof; conjugated to at least one of a permeation enhancer.

In one embodiment, the term "drug reservoir" refers to a composition made to retain and release a conjugate of quetiapine for transdermal delivery, which composition is produced by combining the conjugate of quetiapine and a matrix material. The drug reservoir can be a solid reservoir layer, a solid reservoir adhesive layer, or a liquid reservoir layer containing quetiapine conjugate. In some embodiments, the conjugate of quetiapine reservoir can be a solid reservoir layer of the conjugate of quetiapine in a multilaminate transdermal delivery medical device. When combined with an adhesive, the conjugate of quetiapine reservoir can also be a solid reservoir adhesive layer, which can be used, for example, in a monolith transdermal quetiapine conjugate delivery medical device. The conjugate of quetiapine reservoir can also comprise permeation enhancers, plasticizers, and any other suitable additive, unless otherwise noted.

In certain discrete embodiments, the matrix compositions of the transdermal conjugated quetiapine delivery system can, optionally, also contain agents known to accelerate the delivery of the conjugate of quetiapine through the skin. These agents are referred to as skin penetration enhancers, accelerants, adjuvants, and sorption promoters, and are collectively referred herein as "permeation enhancers." This class of agents includes, but is not limited to those with diverse mechanisms of action including those which have the function of improving the solubility and diffusivity of the conjugate of quetiapine within the multiple polymer and those which improve percutaneous absorption, for example, by changing the ability of the stratum corneum to retain moisture, softening the skin, improving the skin's permeability, acting as penetration assistants or hair follicle openers or changing the state of the skin including the boundary layer. Some of these agents have more than one mechanism of action, but in essence they serve to enhance the delivery of the conjugate of quetiapine, its active metabolites and/or active derivatives.

In another embodiment, the term "permeation enhancer" refers to an agent or a mixture of agents that increases the permeability of the skin to the conjugate of quetiapine, its active metabolite and/or active derivative, their pharmaceutically acceptable salt and/or their combination. In yet another aspect, the term "permeation enhancer" refers to the increase in the permeability of skin to the conjugate of quetiapine, its active metabolite and/or active derivative, their pharmaceutically acceptable salt and/or their combination in the presence of a permeation enhancer as compared to permeability of skin to the conjugate quetiapine, its active metabolite and/or active derivative, their pharmaceutically acceptable salt and/or their combination in the absence of a permeation enhancer.

In one embodiment, the permeation enhancer conjugated to quetiapine, its active metabolite and/or active derivative, their pharmaceutically acceptable salt and/or their combination is at least one of a cross-linked fatty acid. In another embodiment, the permeation enhancer conjugated to quetiapine, its active metabolite and/or active derivative, their pharmaceutically acceptable salt and/or their combination is a short-chain fatty acid such as acetic acid in one embodiment, a medium-chain fatty acid such as capric acid in another embodiment, a long-chain fatty acid such as linoleic acid in another embodiment, or a saturated fatty acid, a monounsaturated fatty acid, a polyunsaturated fatty acid, an acetylenic fatty acid, a substituted fatty acid, a heteroatom containing fatty acid, or a ring containing fatty acid in other discrete embodiments of the permeation enhancer conjugated to quetiapine, its active metabolite and/or active derivative, their pharmaceutically acceptable salt and/or their combination used in the systems and methods described herein. In another embodiment, the term "Fatty acid permeation enhancers" refer to fatty acids of $C_4$-$C_{30}$ in one embodiment, or $C_{10}$-$C_{21}$ in another embodiment that are effective to increase aggregate transdermal delivery of the respective conjugate of quetiapine, its active metabolite and/or active derivative, their pharmaceutically acceptable salt and/or their combination.

In one aspect, the configuration of the transdermal conjugate of quetiapine delivery systems described herein can be in any shape or size as is necessary or desirable. Patch sizes are: from 5 to 60 $cm^2$. In order to deliver quetiapine at the required rate for the desired duration, the loading of quetiapine in the patch should be sufficient to maintain saturation of the drug.

In one embodiment a single dosage unit has a surface area in the range of 3.5 $cm^2$ to deliver between about 25 and about 60 mg of the quetiapine conjugate per day. In order to maintain saturation for seven days, the patch contains between about 175 and about 420 mg of the quetiapine conjugate (7 days×25-60 mg/day) in excess of the quantity needed to saturate the patch with the conjugate of quetiapine. As provided herein, in one embodiment, quetiapine, its active metabolite and/or its active derivative is conjugated to a saturated fatty acid, a monounsaturated fatty acid, a polyunsaturated fatty acid, an acetylenic fatty acid, a substituted fatty acid, a heteroatom containing fatty acid, or a ring containing fatty acid, or in another aspect to a functionalized fatty acid, wherein the functionalized fatty acid is cross-linked, forming a gel matrix, such as a polyunsaturated fatty acid in one embodiment or a mixture of hydroxy fatty acids and dicarboxylic fatty acids in another embodiment. Assuming an acceptable weight for the matrix/quetiapine is 25-40 $mg/cm^2$ it would require a patch of between about 7-11 $cm^2$, or between about 1 and about 2.6 $in^2$ to maintain the desired weekly release rate, since the reservoir matrix, is structurally saturated with the conjugate of quetiapine.

In one embodiment, the conjugate of quetiapine or an active metabolite and/or an active derivative thereof and at least one of a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid, a salt thereof, a derivative thereof or their combination is present in an amount that produces plasma concentrations of quetiapine or its active metabolite and/or active derivative thereof between about 89% and about 115% of the plasma concentrations achieved after oral administration of an amount of between about 1 mg and about 2000 mg per unit dose.

In another aspect, the fatty acid conjugated to quetiapine and/or its active metabolite and/or its active derivative(s) used in the transdermal delivery systems described herein; is at least one of a saturated fatty acid, a monounsaturated fatty acid, a polyunsaturated fatty acid, an acetylenic fatty acid, a substituted fatty acid, a heteroatom containing fatty acid, a ring containing fatty acid, or a cross-linked fatty acid. In another aspect, the fatty acid conjugated to quetiapine and/or its active metabolite and/or its active derivative(s) used in the transdermal delivery systems described herein; is at least one of an alkyl-substituted, hydroxy-substituted, carboxy-substituted, sulfate-substituted, methoxy-substituted, acetoxy-substituted, aldehyde-substituted, halogenated, nitro-substituted, keto-substituted fatty acid, or a fatty acid containing at least one three-membered ring, a fatty acid containing at least one five-membered ring, a fatty acid containing at least one six-membered ring, a fatty acid containing ladderanes, a fatty acid containing at least one furan ring or a combination thereof in other discrete embodiments of the fatty acid conjugated to quetiapine and/or its active metabolite and/or its active derivative(s) used in the transdermal delivery systems described herein.

In one embodiment, the term "cross-linked fatty acid" refers to the insertion of a functional moiety capable of imparting on the underlying fatty acid properties that were not present in the non-functional fatty acid. These functions include in one embodiment, but by no means are limited to; polymerization, cross-linking, ligand attachment site and the like. In another embodiment, the cross-linked fatty acid is selected from the group consisting of any one of the functionalizable fatty acid compounds set forth in Tables II-VII.

In one embodiment, the conjugate of quetiapine transdermal therapeutic system, comprising a drug reservoir comprised essentially of a) a gelling agent; and b) quetiapine, an active metabolite or derivative thereof and therapeutically acceptable salt thereof, and mixtures thereof; conjugated to at least one of a permeation enhancer such as a medium chain fatty acid; further comprise a non-permeable backing and a permeable membrane located between the release matrix and a site of interest on the skin of a subject. In another embodiment backing materials comprise plastic films of polyethylene, vinyl acetate resins, ethylene vinyl acetate (EVA) copolymers, polyvinyl chloride, polyurethane, and the like, metal foils, non-woven fabric, cloth and commercially available laminates. In another aspect, the backing material has a thickness in the range of 2, to 3000 micrometers. In certain embodiments, the backing material is substantially impermeable to the conjugate of quetiapine contained in the reservoir layer. In another embodiment, the backing is a multi-layer polymer film containing a layer of aluminum. In one aspect, the backing material comprises a multilaminate of polyethylene terephthalate (PET) and polyethylene vinyl acetate (PEVA) copolymer. Numerous examples of appropriate backing materials are recognized in the art. In some embodiments, the backing is opaque. Some non-limiting, specific examples of backing materials include: (1) a PET backing material with a sealable layer of EVA (e.g., 12% vinyl acetate, VA) coated on one side of the PET backing material; (2) a film comprising layers of low density PET, nylon, EVA, and ethylene vinyl alcohol; (3) a film comprising layers of low density polyethylene, nylon and EVA; (4) a bilayer film comprising low density polythethylene and nylon; (5) a monolayer of polyethylene; or (6) a monolayer of PET.

In another embodiment, patches provided herein include an outer layer (or "backing layer") that is distal to the skin. A reservoir patch includes in one embodiment a reservoir of the conjugate of quetiapine where the reservoir is defined by the backing layer and a permeable layer of material that contacts the skin and allows the prodrug to pass there through.

In one embodiment, the compositions described herein are used in the transdermal quetiapine conjugate delivery system described herein and are used in the methods provided herein. Accordingly and in another embodiment, provided herein is use of a conjugate of quetiapine transdermal therapeutic system, comprising a drug reservoir comprised essentially of a) a gelling agent that is quetiapine, its active metabolite and/or its active derivative conjugated to a cross-linked functionalized fatty acid capable of forming a gel matrix; and b) quetiapine, an active metabolite or derivative thereof and therapeutically acceptable salt thereof, and mixtures thereof; conjugated to at least one of a permeation enhancer, for the treatment of a neuropsychiatric disorder, such as schizophrenia. In another aspect, the neuropsychiatric disorder is bipolar disorder, obsessive-compulsive disorder, post-traumatic stress disorder, restless legs syndrome, autism, alcoholism, depression, insomnia or Tourette syndrome in other embodiments of the neuropsychiatric disorders using the quetiapine transdermal therapeutic system described herein.

In one embodiment, the conjugate of quetiapine, its antipsychotic-active metabolite and a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid or a combination thereof used in the compositions provided herein, a salt thereof, a derivative thereof or their combination is present in an amount of between about 1 mg and 3000 mg per dose form such as for oral, transdermal, rectal, intrathecal or parenteral administration. In another embodiment, quetiapine or its antipsychotic-active metabolite conjugates, their salts or pharmaceutically acceptable salts are present in the compositions provided herein in an amount that is therapeutically effective. In one embodiment, quetiapine or its antipsychotic-active metabolite conjugates, their salts or pharmaceutically acceptable salts are present in the compositions provided herein in an amount of between about 150 and 800 mg per dose form. In one embodiment, quetiapine or its antipsychotic-active metabolite conjugates, their salts or pharmaceutically acceptable salts are present in the compositions provided herein in an amount of between about 1 and 100 mg per dose form, or between about 100 and 200 mg/dose, or between about 200 and 300 mg/dose, or between about 300 and 400 mg/dose, or between about 400 and 500 mg/dose, or between about 500 and 600 mg/dose, or between about 600 and 700 mg/dose, or between about 700 and 800 mg/dose, or between about 800 and 900 mg/dose, or between about 900 and 1000 mg/dose, or between about 350 and 400 mg/dose, or between about 20 and 30 mg/dose, or between about 50 and 150 mg/dose, or between about 1 and 375 mg/dose, each a discrete embodiment of the amount quetiapine or its antipsychotic-active metabolite conjugates, their salt or pharmaceutically acceptable salt are present in the compositions provided herein. In one embodiment, quetiapine or its antipsychotic-active metabolite conjugates, their salts or pharmaceutically acceptable salts are present in the compositions provided herein in an amount of between about 1000 and 2000 mg per dose form. In another embodiment, quetiapine or its antipsychotic-active metabolite conjugates, their salts or pharmaceutically acceptable salts are present in the compositions provided herein in an amount of between about 1000 and 1250 mg per dose form, or between about 1250 and 1500 mg per dose form, or between about 1500 and 1750 mg per dose form, or between about 1750 and 2000 mg per dose form, or between about 1000 and 1500 mg per dose form, or between about 1500 and 2500 mg per dose form, or between about 1000 and 3000 mg per dose form, or between about 2000 and 3000 mg per dose form, or between about 2500 and 3000 mg per dose form in other discrete embodiments.

Doses of the fatty acid-quetiapine conjugate prodrugs described herein can be higher or lower than doses of unconjugated quetiapine depending on their molecular weight, the respective weight-percentage of quetiapine as part of the whole conjugate or conjugate salt and their bioavailability (with respect to released quetiapine). Dose conversion from quetiapine fumarate to quetiapine prodrug are performed in one embodiment, using the following formula:

$$\text{Dose (QTP prodrug)} = f_{BA} \times [\text{dose(QTP hemifumarate)} \times (\text{molecular weight(QTP prodrug)}/441.95 \text{ g/mol}]$$

Wherein:

QTP=quetiapine $f_{BA}$=correction factor accounting for differences in bioavailability between unmodified quetiapine and the compositions comprising the prodrugs described herein. This correction factor is specific for each prodrug with $f_{BA} \leq 1$ in certain embodiments. In one embodiment, the conjugate of quetiapine, an active metabolite or derivative thereof and a saturated fatty acid, a monounsaturated fatty acid, a polyunsaturated fatty acid, an acetylenic fatty acid, a substituted fatty acid, a heteroatom containing fatty acid, a ring containing, a cross-linked fatty acid or a combination thereof is present in an amount calculated according to the formula provided herein, referred to as "equivalent dose" to certain unconjugated quetiapine doses.

In another aspect, the amount per unit dose is based on the content of quetiapine or active metabolite thereof in the conjugate of quetiapine or an active metabolite and/or an active derivative thereof and at least one fatty acid, a salt thereof, a derivative thereof or their combination.

Quetiapine is a dibenzothiazepine derivative. In pharmacokinetic studies quetiapine is rapidly absorbed after oral administration, with median time to reach maximum observed plasma concentration ranging from 1 to 2 hours. Absolute bioavailability is estimated at 9%, with a relative bioavailability from orally administered tablets compared with a solution of almost 100%. Administration with food other than high-fat foods, has minimal effects on the absorption of the API. The drug is approximately 83% bound to serum proteins. Linear pharmacokinetics is observed in the clinical dose range (up to 375 mg twice daily). The terminal half-life time for the drug's elimination is about 7 hours, with the primary route of elimination being through hepatic metabolism.

In one embodiment, the term "relative bioavailability" refers to $AUC_{(0-\infty)}$ for a specific orally administered composition expressed as a percentage of $AUC_{(0-\infty)}$ for an orally administered solution of the active ingredient at the same dosage rate. The term "$C_{max}$" refers to the maximum observed blood plasma concentration or the maximum blood plasma concentration calculated or estimated from a concentration/time curve, and in one aspect, is expressed in units of ng/ml. The term "$T_{max}$" refers to the time after administration at which $C_{max}$ occurs, and is expressed in units of hours (h).

In one embodiment, relative bioavailability of the compositions described herein is increased by between about 9 and 100% when administered orally compared with oral administration of unconjugated quetiapine, an active metabolite and/or an active derivative thereof. In another embodiment, the relative bioavailability is increased by between about 25 and 100%, or between about 50 and 100%, or between about 75 and 100%, or between about 100 and 125%, or between about 125 and 150%, or between about 150 and 175%, or between about 175 and 200%, or between about 9 and 25%, when administered orally compared with oral administration of unconjugated quetiapine, an active metabolite and/or an active derivative thereof in other discrete embodiments.

Quetiapine is metabolized in one embodiment by cytochrome P450 (CYP) 3A4 and/or 2D6 in certain other embodiments. Eleven metabolites were identified as formed through hepatic conversion, with three of those found to be pharmacologically active. In one embodiment, the metabolites are conjugated to the fatty acids described herein and are administered either alone or in combination with other quetiapine conjugate compositions described herein and used in the methods and systems described. Accordingly, in one embodiment, provided herein is a composition for treating a psychiatric disorder in a subject, comprising a conjugate of 7-hydroxy-quetiapine (7-OH-QTP) represented by the structure of Formula II:

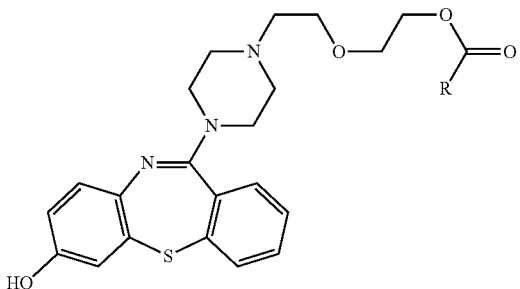

(II)

and a fatty acid, a salt thereof, a derivative thereof or their combination. In another embodiment, provided herein is a composition for treating a psychiatric disorder in a subject, comprising a conjugate of N-desalkyl-quetiapine (norQTP) represented by the structure of Formula III:

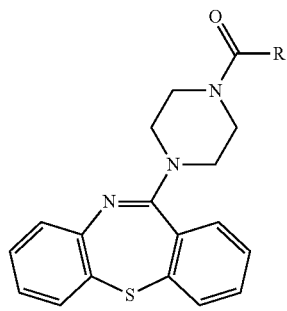

(III)

and a fatty acid, a salt thereof, a derivative thereof or their combination. In another embodiment, provided herein is a composition for treating a psychiatric disorder in a subject, comprising a conjugate of 7-hydroxy-N-desalkyl-quetiapine (7-OH-norQTP) represented by the structure of Formula IV:

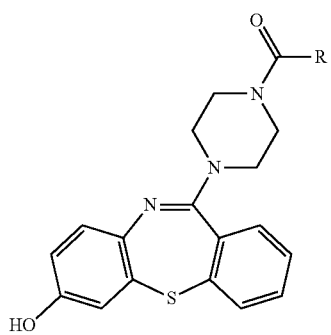

(IV)

and an fatty acid, a salt thereof, a derivative thereof or their combination.

In one embodiment, oral clearance of unconjugated quetiapine declines with age. In another embodiment, relative bioavailability of fatty acid-quetiapine conjugates is higher at every age, thereby leading to reduced dosage requirements for every indication and minimizing side-effects. Since quetiapine is primarily metabolized by CYP3A4 and/or CYP2D6, dosage adjustment may be necessary in another embodiment when coadministered with phenytoin, thioridazine, retinoic acid, rifampicin, ketoconazole, carbamazepine or other potent CYP3A4 agonists, antagonists or modulators. Similarly, dosage adjustment may be necessary in another embodiment when coadministered with dextromethorphan, aripiprazole, donepezil, paroxetine, lasofoxifene, risperidone or other potent CYP2D6 agonists, antagonists or modulators. In one embodiment, the choice of fatty-acid conjugated to quetiapine will affect the dosage adjustment necessary.

Advantages

Conjugation of quetiapine or an active metabolite thereof to fatty acids as described herein, has a number of advantages that may include:
 1. Reduced interindividual variability in plasma concentrations vs. free quetiapine
 2. Increased bioavailability
 3. Improved side-effect profile
 4. Less potentially toxic metabolites
 5. Less inactive metabolites
 6. Improved solubility in organic solvents 7. Reduced potential for drug abuse In one embodiment, the compositions comprising quetiapine conjugated to a fatty acid, further comprise a carrier, excipient, lubricant, flow aid, processing aid or diluent, wherein said carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetener, a film forming agent, or any combination thereof.

In one embodiment, the composition is a controlled release composition. In another embodiment, the composition is an immediate release composition. In one embodiment, the composition is a liquid dosage form. In another embodiment, the composition is a solid dosage form.

In one embodiment, the term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of the fatty acid-quetiapine conjugates described herein, are prepared in another embodiment, from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, in another embodiment, the appropriate acid or base with the compound.

In one embodiment, the term "pharmaceutically acceptable carriers" includes, but is not limited to, 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In one embodiment the concentration of phosphate buffer used as a pharmaceutically acceptable carrier is between about 0.01 to about 0.1M, or between about 0.01 to about 0.09M in another embodiment, or between about 0.01 to about 0.08M in another embodiment, or between about 0.01 to about 0.07M in another embodiment, or between about 0.01 to about 0.06M in another embodiment, or between about 0.01 to about 0.05M in another embodiment, or between about 0.01 to about 0.04M in another embodiment, or between about 0.01 to about 0.03M in another embodiment, or between about 0.01 to about 0.02M in another embodiment, or between about 0.01 to about 0.015 in another embodiment.

The pharmaceutical preparations comprising the compositions used in one embodiment in the methods provided herein can be prepared by dissolving, mixing, granulating, or tablet-forming processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water for injection and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions. In one embodiment, using fatty acid conjugates, increases solubility or dispersibility of quetiapine, its active metabolite and/or derivative in the oily vehicles described herein.

In addition, the compositions described in the embodiments provided herein, can contain minor amounts of auxiliary substances such as wetting or emulsifying agents, pH buffering agents which enhance the effectiveness of the active ingredient.

The fatty acid-quetiapine conjugate described herein is administered in another embodiment, in a therapeutically effective amount. The actual amount administered, and the rate and time course of administration, will depend in one embodiment, on the nature and severity of the condition being treated. Prescription of treatment, e.g., decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

The compositions of the present invention are formulated in one embodiment for oral delivery, wherein the active compounds may be incorporated with excipients and used in the form of ingestible tablets, buccal tablets, troches, capsules, elixirs, suspensions, syrups, wafers, and the like. The tablets, troches, pills, capsules and the like may also contain the following: a sweetening agent, such as sucrose, lactose or saccharin that may be added or a flavoring agent, such as peppermint, oil of wintergreen, or cherry flavoring. When the dosage unit form is a capsule, it may contain, in addition to materials of the types described hereinabove, a liquid carrier. Various other materials may be present as coatings or to otherwise modify the physical form of the dosage unit. For instance, tablets, pills, or capsules may be coated with shellac, sugar, or both. Syrup or elixir may contain sucrose as the active sweetening agent, methyl and propylparabens as preservatives, a dye and flavoring, such as cherry or orange flavor. In addition, the API may be incorporated into sustained-release, pulsed release, controlled release or postponed release preparations and formulations.

In another embodiment, the term "dosage unit" refers to the portion of a pharmaceutical composition that contains a single unit dose of the active ingredient. For purposes of the disclosure presented herein, a dose unit can be in the form of a discrete article such as a tablet or capsule, or can be a measurable volume of a solution, suspension or the like containing a unit dose of the active ingredient. The term "unit dose" refers in one embodiment to an amount of active ingredient intended for a single oral administration to a subject for treatment of a psychiatric condition or disorder. Treatment of a psychiatric condition or disorder, comprising mediating or binding of a dopamine and/or serotonin and/or histamine receptor, may require periodic administration of unit doses of the compositions described herein, for example one unit dose two or more times a day, one unit dose with each meal, one unit dose every four hours or other interval, or only one unit dose per day.

Controlled or sustained release compositions include formulations in lipophilic depots (e.g., fatty acids, waxes, oils). Also comprehended by the invention are particulate compositions coated with polymers (e.g., poloxamers or poloxamines). In another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 [1984]). Other controlled release systems are discussed in the review by Langer (Science 249:1527-1533 [1990]).

In one embodiment, the carriers for use within such compositions are biocompatible, and/or biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture, lower pH or temperature threshold in other discrete embodiments. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated, suppressed or inhibited.

In one embodiment, the term "administering" refers to bringing a subject in contact with the compositions provided herein. For example, in one embodiment, the compositions provided herein are suitable for oral administration, whereby bringing the subject in contact with the composition comprises ingesting the compositions. A person skilled in the art would readily recognize that the methods of bringing the subject in contact with the compositions provided herein, will depend on many variables such as, without any intention to limit the modes of administration; age, pre-existing conditions, other agents administered to the subject, the severity of symptoms, subject weight or propensity to gain weight, refraction to other medication and the like. In one embodiment, provided herein are embodiments of methods for administering the compounds of the present invention to a subject, through any appropriate route, as will be appreciated by one skilled in the art.

Methods of Synthesis

A general synthetic scheme for the synthesis of a prodrug of this invention typically consists of the following steps:
1. Protection of substituents on the fatty acid, if applicable.
2. Activation of the carboxylic group, if not already in activated form.
3. Addition of activated fatty acid to quetiapine or vice versa in the presence of base
4. Removal of any protecting groups, if applicable.

Accordingly and in one embodiment, provided herein is a method of conjugating quetiapine or an active metabolite and/or an active derivative thereof and at least one fatty acid, comprising the steps of: in the presence of a base, attaching a carboxyl activated fatty acid to quetiapine or its active metabolite and/or derivative; followed by deprotecting the optionally protected fatty acid moiety, thereby conjugating quetiapine or an active metabolite and/or an active derivative thereof and at least one fatty acid The carboxylic acid group of the fatty acid is activated in one embodiment in order to react with quetiapine to produce appreciable amounts of conjugate. The fatty acids can be activated in another embodiment, by synthesizing esters of N-hydroxy succinimide (NHS). Other activating agents include but are not limited to the following: N,N'-dicyclohexylcarbodiimide (DCC), N-(3-dimethylaminopropyl)-N'-ethylcarbodiimide (EDCI), N,N'-diisopropyl-carbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidino-phosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl)uronium tetrafluoroborate (TSTU) or other aminium-based reagents.

It may be necessary to attach one or more protecting groups to any additional reactive functional groups that may interfere with the coupling to quetiapine. Any suitable protecting group may be used depending on the type of functional group and reaction conditions. In one embodiment a protective group is for a thiol, hydroxy, amino or carboxyl group used in common preparations of the conjugated prodrugs described herein. Suitable protecting group examples include but are not limited to: acetyl (Ac), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, etc). In another embodiment, the fatty acid residue protecting group is acetyl, propionyl, butyryl, phenylacetyl, benzoyl, toluyl, phenoxyacetyl (POA), methoxycarbonyl, ethoxycarbonyl, 2,2,2-trichloro-ethoxycarbonyl, 2-iodoethoxycarbonyl, 4-methoxybenzyloxycarbonyl, 4-methoxy-2,3,6-trimethyl-benzenesulfonyl (Mtr), 2,2,4,6,7-pentamethyldihydrobenzofuran-5-sulfonyl (Pbf) or 2,2,5,7,8-pentamethyl-chroman-6-sulfonyl (Pmc).

A base may be required at any step of the synthesis of fatty acid conjugates of quetiapine. Suitable bases include but are not limited to 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert-butoxide (e.g., potassium tert-butoxide), any alkali metal hydride (e.g., sodium hydride), any alkali metal alkoxide (e.g., sodium methoxide), triethylamine or any other tertiary amine.

An acid may be required to remove certain protecting groups. Suitable acids include but are not limited to hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid.

Appropriate solvents that can be used for any reaction in the synthetic scheme of any fatty acid conjugate of quetiapine include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert-butyl ether (MTBE), isopropanol, isopropyl acetate, diisopropyl ether, tetrahydrofuran, toluene, xylene or water.

In one embodiment, the compounds conjugated using the methods provided herein, are used in the compositions, transdermal delivery systems and methods described herein. Accordingly, and in another embodiment, provided herein is a quetiapine, its active metabolite and/or derivative; conjugated to a saturated fatty acid, a monounsaturated fatty acid, a polyunsaturated fatty acid, an acetylenic fatty acid, a substituted fatty acid, a heteroatom containing fatty acid, a ring containing fatty acid, a cross-linked fatty acid, or a combination thereof synthesized by attaching a fatty acid in the presence of a base to quetiapine or its active metabolite and/or derivative; followed by optionally deprotecting any functional moiety on the fatty acid moiety, thereby conjugating quetiapine, an active metabolite and/or an active derivative thereof and a fatty acid.

In one embodiment, the compositions described herein are used to carry out the methods provided herein.

In one embodiment, the psychiatric disorder sought to be treated using the compositions provided herein is bipolar disorder (BPD) and the inpatient receives conjugated valproate-quetiapine at an equimolar dose in the amount of 375 mg daily of unconjugated quetiapine, corresponding to a dose of over 375 mg daily due to the higher bioavailability of the conjugated quetiapine as described herein, leading to a larger difference and shorter duration in depressive symptoms on admission and at discharge using the Beck-Rafaelsen Mania Scale (MAS) and/or the Montgomery Asberg depression rating scale (MADRS), respectively.

In another aspect, valproic acid is becoming an increasingly common agent to be taken in overdose, with a sharp rise in incidence over the last 5 years (e.g., divalproex). This is likely to be a result of the broadening clinical uses of valproate, including its use as a mood stabilizer in patients with bipolar and affective disorders. Valproic acid is FDA approved for the treatment of acute manic episodes. Its response rate in acute mania is around 50%, compared to a placebo effect of 20-30%. Patients respond relatively rapidly (within 1-2 weeks and often a few days). Valproate appears to have a more robust antimanic effect than lithium in rapid cycling and mixed episodes. Concerning bipolar depression, there is inconsistent data regarding its efficacy with some data suggesting reduced effectiveness compared to mania (response rate close to 30%). Although valproate seems to have significant prophylactic antimanic properties, its prophylactic antidepressant ones are low to moderate. In one embodiment, conjugating valproic acid to quetiapine as described herein, creates a novel mutual prodrug API that increases the efficacy of valproate AND quetiapine as a single API mood stabilizer, reduces the risk of overdosing or their combination. Accordingly and in one embodiment, provided herein is the use of quetiapine, its active metabolite and/or active derivative, conjugated to valproic acid in a composition for the treatment of disorders including, but not limited to, absence seizures, tonic-clonic seizures (grand mal), complex partial seizures, juvenile myoclonic epilepsy; seizures associated with Lennox-Gastaut syndrome, myoclonus, rapid cycling bipolar disorder, bipolar disorder associated mania, bipolar disorder associated depression or their combination.

The term "mutual prodrug" in one embodiment is interchangeable with the term "codrug" referring in one embodiment to a chemically modified therapeutic agent, which consists of two drugs covalently linked together in order to modulate the drug delivery, metabolism, stability or a combination thereof of one or both drugs. In another embodiment, the codrug consists of two pharmacologically active drugs that are coupled together in a single molecule, so that each drug acts as a promoiety for the other. In one embodiment, the advantage of using the transdermal valproate-quetiapine codrug; which can undergo bioconversion to the active parent drugs, is that the skin irritation and allergenic potential of the codrug should only mirror the profile of the active parent drugs, without the added toxicities of additional penetration enhancers or active transport devices. Because the skin and plasma have an abundance of esterase enzymes, codrugs with esterase-susceptible linkages such as the valproate-quetiapine conjugate provided herein, can be cleaved by these enzymes to release the active parent drugs in the CS tissue and plasma.

Therapeutically effective serum concentrations of valproic acid range between 50 and 150 mg/mL. Side-effects from administration of valproic acid comprise gastrointestinal symptoms in one embodiment, or sedation, tremor, weight gain, hair loss, ataxia, dysarthria or persistent elevation of hepatic transaminases in other discrete embodiments of the adverse side-effects capable of being eliminated, ameliorated or reduced using quetiapine, its active metabolite and/or active derivative, conjugated to valproic acid compositions provided herein.

In another embodiment, the psychiatric disorder sought to be treated using the compositions provided herein is schizophrenia, and the inpatient receives conjugated quetiapine at an equimolar dose in the amount of 450 mg daily of unconjugated quetiapine, corresponding to a dose of over 450 mg daily due to the higher bioavailability of the conjugated quetiapine as described herein, leading to a larger difference and shorter duration in depressive symptoms on admission and at discharge using Brief Psychiatric Rating Scale (BPRS), Clinical Global Impression (CGI), Positive And Negative Syndrome Scale (PANSS) and the like. Using the compositions described herein, results in another embodiment in increased intervals between psychotic episodes, decrease in severity of the episodes and a lesser loss in cognitive abilities following an episode.

In one embodiment, provided herein is a method of treating a psychiatric disorder involving the binding to dopamine receptor(s), serotonin receptor(s), norepinephrine receptor(s) or a combination and/or permutation thereof in a subject, comprising the step of administering to the subject a composition comprising a therapeutically effective amount of quetiapine, an active metabolite and/or an active derivative thereof, conjugated to at least one fatty acid, a pharmaceutically acceptable salt or derivative thereof, thereby binding to dopamine receptor(s), serotonin receptor(s), or norepinephrine receptor(s) or a combination and/or permutation thereof.

In another embodiment, provided herein is a method of treating schizophrenia or bipolar disorder in a subject in need thereof, comprising the step of administering to the subject a composition comprising a therapeutically effective amount of quetiapine, an active metabolite and/or an active derivative thereof, conjugated to at least one fatty acid, a pharmaceutically acceptable salt or derivative thereof, thereby binding to dopamine receptor(s), serotonin receptor(s), or both.

In another embodiment, due to the higher relative bioavailability, the unit dose used for treating the disorders described herein will be adjusted downward, leading to a decrease in number and severity of side-effects.

In one embodiment, the disorder requiring the binding to dopamine receptor(s), serotonin receptor(s), or both in a subject is obsessive-compulsive disorder (OCD), post-traumatic stress disorder (PTSD), restless legs syndrome, autism, alcoholism, depression, insomnia, hyperprolactinemia or Tourette syndrome.

By way of example, restless leg syndrome (RLS) has been treated with non-ergot dopamine agonists, with quetiapine showing remarkable efficacy. In one embodiment, provided herein is a method of treating RLS in a subject in need thereof, comprising the step of orally administering to the subject a therapeutically effective amount of a composition comprising quetiapine, an active metabolite and/or active derivative thereof conjugated to a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof, a pharmaceutically acceptable salt thereof or their combination.

Likewise and in another embodiment, post-traumatic stress disorder (PTSD) refers in one embodiment to a chronic mental illness, causing occupational disability, psychiatric and medical morbidity and severe psychosocial distress. The prevalence of PTSD in the general population in the U.S. was estimated to be 7.8% in 2006. Core symptoms of PTSD include recurrent re-experiencing of the trauma in the form of intrusive memories, nightmares and flashbacks; avoidant behaviors; and autonomic arousal. In addition to the core PTSD symptoms, patients with PTSD also exhibit irritability, impulsivity, depression and aggression. PTSD is often difficult to treat, with recent initiatives focusing on the role of serotonin in the neuroregulation of PTSD. The neurotransmitter serotonin influences mood, aggression, arousal, anxiety, sleep, learning, nociception, fear and appetite. Likewise, dopamine neurotransmission dysfunction has been shown to be responsible for symptoms such as paranoia, hallucinations, increased startle response and their combination. Physiologically, the density of platelet serotonin-uptake sites, as determined by paroxetine binding, was significantly decreased in patients with PTSD, compared with normal controls. Clinical studies showed the benefits of treatment of PTSD symptoms with a $5-HT_{1A}$ partial agonist, of which quetiapine metabolite N-desalkylquetiapine is one.

In one embodiment, the term "treating" refers to abrogating, substantially inhibiting, slowing or reversing the progression of a disease, substantially ameliorating clinical symptoms of a disease or substantially preventing or delaying the appearance of clinical symptoms of a disease.

In one embodiment, the compositions provided herein, which in another embodiment are used in the methods described herein; are administered to a subject in need thereof as part of a combination therapy with other medication that is specific for the indication sought to be treated. A person skilled in the art would readily recognize that combination therapy as described in the methods and compositions provided herein, could be administered either simultaneously or consecutively and so long as they are administered for the same indication, would be encompassed by the description provided herein.

Accordingly and in certain embodiments, lithium and/or divalproex are used as adjunct therapies with the compositions provided herein.

Another embodiment provided herein is the use of a therapeutically effective amount of a conjugate of quetiapine, its active metabolite and/or active derivative; and a saturated fatty acid, a monounsaturated fatty acid, a polyunsaturated fatty acid, an acetylenic fatty acid, a substituted fatty acid, a heteroatom containing fatty acid, a ring containing fatty acid or a combination thereof in a medicament for the treatment of a disorder associated with serotonin, dopamine or norepinephrine dysfunction in a subject in need thereof.

In the present specification, use of the singular includes the plural except where specifically indicated.

In one embodiment, the term "subject" refers to a mammal including a human in need of therapy for, or susceptible to, a condition or its sequelae. The subjects may include dogs, cats, pigs, cows, sheep, goats, horses, rats, mice and humans. The term "subject" does not exclude an individual that is normal in all respects. In one embodiment, the subject is a human subject.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Example 1: Oral Pharmacokinetic Data

Prodrug conjugates described herein were dosed as oral solutions in rats and compared to an equimolar solution of quetiapine dihydrochloride. Although the commercial form of quetiapine (Seroquel®) is a fumarate salt, the dihydrochloride salt was used as comparator because the fumarate is not soluble enough to be dosed efficiently via oral gavage in rats.

Generally and as shown in FIGS. 1-4, plasma concentrations of quetiapine released from the prodrugs described herein were compared to plasma concentrations generated by an equimolar amount of quetiapine hydrochloride salt. Overall, plasma concentrations of released quetiapine varied depending on the attached fatty acid. Exposure ranged from 34-121%-AUC compared to quetiapine hydrochloride salt.

Example 2: General Synthesis of Fatty Acid-Quetiapine Conjugates

Figure 5:
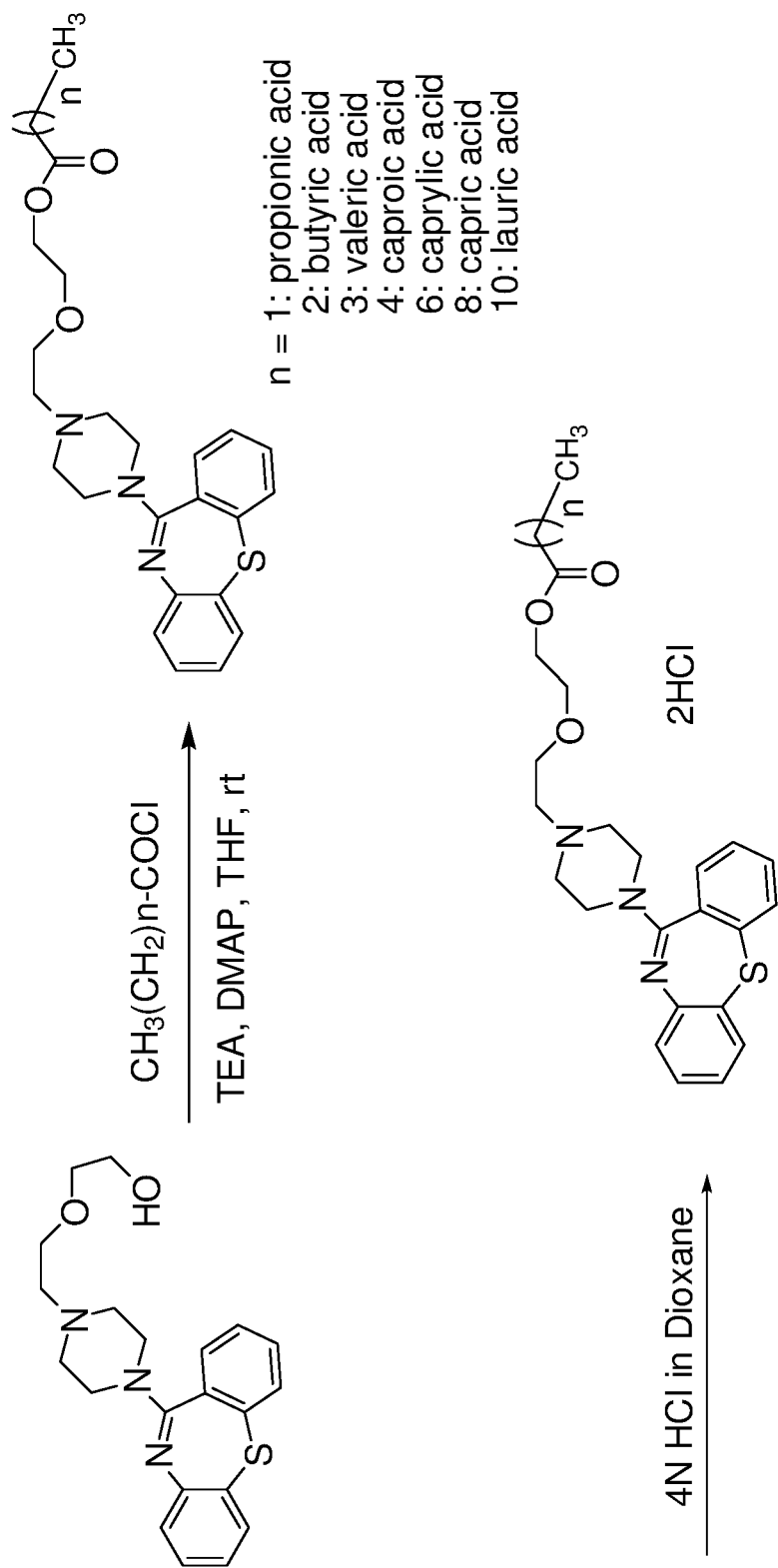
FIG. 5 shows a schematic of the process of synthesis of fatty acid-Quetiapine conjugate.

A general synthetic scheme for the synthesis of a prodrug of this invention typically consists of the following steps (See FIG. 5):
1. Protection of a functional moiety on the fatty acid, if applicable.
2. Activation of the carboxylic group, if not already in activated form.
3. Addition of activated fatty acid to quetiapine or vice versa in the presence of base
4. Removal of protecting groups on functional moieties of the fatty acid, if applicable.

To a solution of quetiapine freebase (1 mmol) in anhydrous THF (20 mL) was added TEA (3 mmol) and DMAP (0.1 mmol). The solution was stirred and the fatty acid chloride (1.5 mmol) was added drop wise at room temperature. After 2-6 hours, depending on the fatty acid derivative, solvents were evaporated to dryness and the residue was dissolved in ethyl acetate (400 mL). The organic phase was washed with aqueous $NH_4Cl$ (2×250 mL) and aqueous $NaHCO_3$ (2×250 mL), dried over anhydrous $Na_2SO_4$ and evaporated to dryness to yield the fatty acid-quetiapine conjugate.

The conjugate was converted to its hydrochloride salt by stirring with 4 N HCl in dioxane for 15 min. at room temperature and evaporating the solvent to dryness. The residue was triturated with IPAc and the precipitate was filtered and dried to yield the hydrochloride salt of the fatty acid-quetiapine conjugate.

Having described certain embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

The invention claimed is:

1. A composition comprising 2-(2-(4-(dibenzo[b,f][1,4] thiazepin-11-yl)piperazin-1-yl)ethoxy)ethanol (quetiapine) conjugated to caprylic acid, a salt of the conjugate, or a combination thereof, and a pharmaceutically acceptable carrier.

2. The composition of claim 1, wherein the salt is pharmaceutically acceptable.

3. The composition of claim 1, wherein the composition has a higher relative bioavailability than non-conjugated quetiapine when administered orally to a subject.

4. The composition of claim 2, wherein the salt of the conjugate is selected from the group consisting of acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, and mixtures thereof.

5. The composition of claim 1, wherein the composition is formulated for oral, sublingual, transdermal, suppository, parenteral, or intrathecal administration.

6. The composition of claim 5, wherein the composition is formulated for oral administration is selected from the group consisting of a tablet, capsule, caplet, pill, powder, troche, lozenge, slurry, liquid solution, suspension, emulsion, elixir, dragee, gel, syrup, granule, wafer, and oral thin film (OTF).

7. The composition of claim 1, wherein the conjugate of quetiapine is present in an amount per unit dose of between about 1 mg and about 2000 mg per unit dose wherein the amount per unit dose is based on the content of quetiapine.

8. The composition of claim 7, wherein the conjugate of quetiapine is present in an amount per unit dose of between about 150 mg and about 800 mg per unit dose wherein the amount per unit dose is based on the content of quetiapine.

9. The composition of claim 3, wherein the subject is a mammal subject.

10. The composition of claim 9, wherein the subject is a human subject.

11. The composition of claim 1, further comprising one or more of: lithium, divalproex, adjuvants, antiadherents, binders, coatings, disintegrants, fillers, flavors and colors, glidants, lubricants, preservatives, sorbents, sweeteners, or a combination thereof.

12. A compound having the following structure:

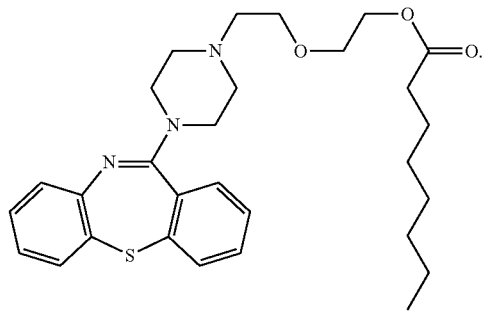 [SMILES: CCCCCCCC(=O)OCCOCCN1CCN(C2=Nc3ccccc3Sc3ccccc32)CC1]

13. A composition comprising the compound of claim 12, a salt of the compound or a combination thereof.

14. The composition of claim 13, wherein the salt is pharmaceutically acceptable.

15. The composition of claim 13, wherein the composition has a higher relative bioavailability than non-conjugated quetiapine when administered orally to a subject.

16. The composition of claim 14, wherein the salt of the conjugate is selected from the group consisting of acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, am inosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, and mixtures thereof.

17. The composition of claim 13, wherein the composition is formulated for oral, sublingual, transdermal, suppository, parenteral, or intrathecal administration.

18. The composition of claim 17, wherein the composition is formulated for oral administration is selected from the group consisting of a tablet, capsule, caplet, pill, powder, troche, lozenge, slurry, liquid solution, suspension, emulsion, elixir, dragee, gel, syrup, granule, wafer, and oral thin film (OTF).

19. The composition of claim 13, wherein the conjugate of quetiapine is present in an amount per unit dose of between about 1 mg and about 2000 mg per unit dose wherein the amount per unit dose is based on the content of quetiapine.

20. The composition of claim 19, wherein the conjugate of quetiapine is present in an amount per unit dose of between about 150 mg and about 800 mg per unit dose wherein the amount per unit dose is based on the content of quetiapine.

21. The composition of claim 15, wherein the subject is a mammal subject.

22. The composition of claim 21, wherein the subject is a human subject.

23. The composition of claim 13, further comprising one or more of: lithium, divalproex, adjuvants, antiadherents, binders, coatings, disintegrants, fillers, flavors and colors, glidants, lubricants, preservatives, sorbents, sweeteners, or a combination thereof.

* * * * *